US00RE48189E

(19) United States
(12) Reissued Patent
Kuwano et al.

(10) Patent Number: US RE48,189 E
(45) Date of Reissued Patent: Sep. 1, 2020

(54) SAMPLE PROCESSING APPARATUS

(71) Applicant: Sysmex Corporation

(72) Inventors: Keisuke Kuwano, Hamburg (DE); Shunsuke Ariyoshi, Hyogo (JP); Tomomi Sugiyama, Hyogo (JP)

(73) Assignee: Sysmex Corporation, Kobe-Shi, Hyogo (JP)

(21) Appl. No.: 14/991,498

(22) Filed: Jan. 8, 2016

Related U.S. Patent Documents

Reissue of:
(64) Patent No.: 8,706,303
Issued: Apr. 22, 2014
Appl. No.: 13/460,004
Filed: Apr. 30, 2012

(30) Foreign Application Priority Data

May 2, 2011 (JP) ..... 2011-103235

(51) Int. Cl.
*G01N 35/00* (2006.01)
*G05B 21/00* (2006.01)

(52) U.S. Cl.
CPC . *G01N 35/00663* (2013.01); *G01N 35/00584* (2013.01); *G01N 2035/009* (2013.01); *G01N 2035/00673* (2013.01); *G01N 2035/00891* (2013.01)

(58) Field of Classification Search
CPC ..... G01N 35/00663; G01N 35/00584; G01N 2035/00673; G01N 2035/009; G01N 2035/00891
See application file for complete search history.

(56) References Cited

U.S. PATENT DOCUMENTS

| | | | | |
|---|---|---|---|---|
| 7,707,010 | B2 * | 4/2010 | Wakamiya ..... | G01N 35/00722 702/187 |
| 8,010,323 | B2 | 8/2011 | Naito | |
| 2005/0177341 | A1 | 8/2005 | Wada | |
| 2007/0078631 | A1 * | 4/2007 | Ariyoshi et al. ..... | 702/189 |
| 2007/0124265 | A1 | 5/2007 | Hebbani et al. | |
| 2007/0174653 | A1 | 7/2007 | Berman et al. | |
| 2007/0233303 | A1 * | 10/2007 | Naito ..... | G01N 35/00584 700/108 |
| 2010/0238043 | A1 | 9/2010 | Wakamiya et al. | |

FOREIGN PATENT DOCUMENTS

| | | | |
|---|---|---|---|
| CN | 1659561 | A | 8/2005 |
| CN | 101393226 | A | 3/2009 |
| EP | 1 840 576 | A2 | 10/2007 |
| EP | 2 040 081 | A2 | 3/2009 |
| JP | 10-31795 | A | 2/1998 |
| JP | 2000-97946 | A | 4/2000 |
| JP | 2003-194702 | A | 7/2003 |
| JP | 2003-232797 | A | 8/2003 |
| JP | 2006-133892 | A | 5/2006 |
| JP | 2007-271334 | A | 10/2007 |
| JP | 2009-74887 | A | 4/2009 |
| JP | 2009-229430 | A | 10/2009 |
| JP | 2010-217039 | A | 9/2010 |

OTHER PUBLICATIONS

Manual, PDF manual of "DocuPrint 3100 DocuPrint 3000 Book to Respond to Study and Trouble", *Fuji Xerox Co., Ltd.*, Oct. 2010, 3 pages. URL: https://www.fujixerox.co.io/support/manual/printer/dp_3000s/manu.html (Office Action in corresponding Japanese Application No. 2015-231185 is attached to provide a concise explanation in the English language).

* cited by examiner

*Primary Examiner* — Krisanne M Jastrzab
(74) *Attorney, Agent, or Firm* — Brinks Gilson & Lione

(57) ABSTRACT

The present invention is a sample processing apparatus. The apparatus includes: a sample processing unit configured to process a sample; a display; a memory for storing an electronic manual for the sample processing apparatus; and a controller that is capable of showing a relevant part of the electronic manual on the display when a trouble has occurred in the sample processing unit, the relevant part of the electronic manual describing an operation procedure to deal with the trouble.

24 Claims, 21 Drawing Sheets

FIG. 8A

Chapter 13 Conserving and replacing supplies

2 Opening the front cover.
open upward completely.
The cover may fall.

3 Loosen the cover locking screw of the detector.

4 Remove the cover.
Lift upward and pull forward.

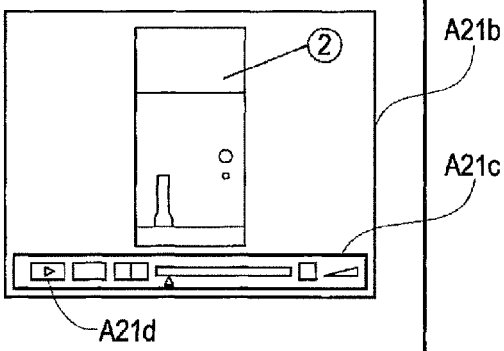

5 Turn the chamber cover in the arrow direction.

6 Immerse the brush for removing blockage in CELL CLEAN, lightly wet wipe the detector plate.

Comment:

· Wipe CELL CLEAN with a tissue when dirty.
· Rinse the brush thoroughly after use.

SAMPLE PROCESSING APPARATUS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

RELATED APPLICATIONS

This application claims priority under 35 U.S.C. §119 to Japanese Patent Application No. 2011-103235 filed on May 2, 2011, the entire content of which is hereby incorporated by reference.

BACKGROUND OF THE INVENTION

1. Field of the Invention

The present invention relates to a sample processing apparatus for processing a sample such as blood.

2. Description of the Related Art

Currently, sample processing apparatuses for processing clinical samples such as blood and urine are used in clinical facilities. When trouble occurs in such sample processing apparatuses, a structure is required to smoothly deal with the trouble since the processing of samples is suspended.

Japanese Patent Application Publication No. 2003/232797 discloses an automatic blood cell analyzer capable of showing on a display a help dialog that includes an OK button and error list when trouble occurs in the measuring unit. In this apparatus, when a specific error is selected from the displayed error list and the OK button is pressed, a suitable recovery process relating to the error is executed or a screen required for the recovery process is shown on the display. When a specific error is selected from the error list, a description of the error and the method of recovering from the error are shown in the action field of the help dialog. For example, when pressure trouble occurs in the measuring unit and is selected from the error list, a [Please adjust pressure] message is displayed in the action field as the method of recovering from the pressure trouble.

In the apparatus disclosed in Japanese Patent Application Publication No. 2003/232797, a user who is unfamiliar with the operation of the apparatus may not be able to adequately understand the proper sequence of operation to deal with the trouble. For example, the specific operation sequence needed to adjust the pressure may not be understood from the [Please adjust pressure] message that is displayed as the method for dealing with the trouble. Therefore, the user must take the time and effort to look up the relevant part describing the method for dealing with the trouble in operating manual of the apparatus stored as a booklet in the facility.

SUMMARY OF THE INVENTION

The scope of the present invention is defined solely by the appended claims, and is not affected to any degree by the statements within this summary.

A first aspect of the present invention is a sample processing apparatus, comprising: a sample processing unit configured to process a sample; a display; a memory for storing an electronic manual for the sample processing apparatus; and a controller that is capable of showing a relevant part of the electronic manual on the display when a trouble has occurred in the sample processing unit, the relevant part of the electronic manual describing an operation procedure to deal with the trouble.

BRIEF DESCRIPTION OF THE DRAWINGS

FIGS. 8A through 8D show the displayed content of the video display region and the page of the electronic manual that includes video of the present embodiment;

DETAILED DESCRIPTION OF THE PREFERRED EMBODIMENT

The present embodiment applies the present invention to a sample processing apparatus for examining and analyzing blood.

The sample processing apparatus of the present embodiment is described below with reference to the accompanying drawings.

Figure 1:
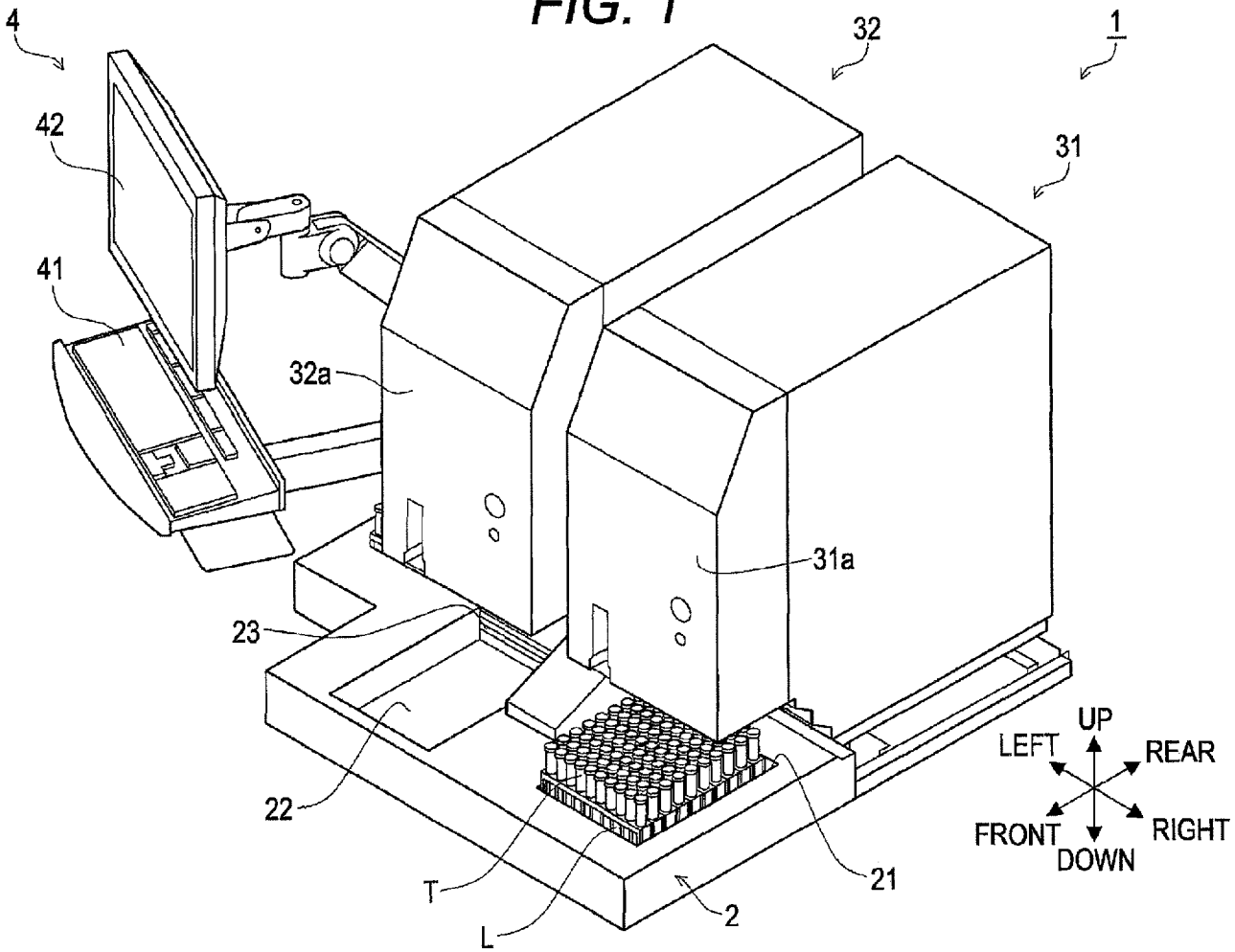
FIG. 1 is a perspective view showing the exterior of an embodiment of a sample analyzer.

FIG. 1 is a perspective view showing the exterior of a sample processing apparatus 1. The sample processing apparatus 1 of the present embodiment is configured by a transport unit 2, measuring units 31 and 32, and an information processing unit 4.

The transport unit 2 is arranged in front of the measuring units 31 and 32, and includes a right table 21, left table 22, and a rack transporter 23 connecting the right table 21 and the left table 22. The right table 21 and the left table 22 can accommodate a plurality of sample racks L, each of the racks L being capable of holding ten sample containers T.

The transport unit 2 accommodates a sample rack L loaded on the right table 21 by the user. The transport unit 2 moves the sample rack L accommodated on the right table 21 to a predetermined position of the rack transporter 23 so as to supply the sample containers T to the measuring units 31 and 32. The transport unit 2 also collects the sample rack L on the rack transport 23 to the left table 22.

Barcode labels respectively adhered to the sample rack L and the sample containers T are read by the barcode reader 203 (refer to FIG. 2) of the transport unit 2 at a predetermined position of the rack transporter 23.

The measuring unit 31 performs processing of the sample container T on the rack transport 23 positioned in front of the unit. That is, the measuring unit 31 removes the sample container T from the sample rack L and moves it into the measuring unit 31 via a hand member (not shown in the drawing), and the sample contained in the sample container T is measured within the measuring unit 31. When the measurement is completed, the measuring unit 31 returns the sample container T to the holder of the original sample rack L. The measuring unit 32 performs measurements of samples identically to measuring unit 31.

The measuring units 31 and 32 respectively have a cover 31a and 32a at the front side of the apparatus. The user can replace reagent in the measuring units 31 and 32, and remove RBC (described later) sample containers by opening the covers 31a and 32a.

The information processing unit 4 has an input section 41 and a display 42. The information processing unit 4 is connected to the transport unit 2, measuring units 31 and 32, and a host computer (not shown in the drawing) so as to be capable of communications through a communication network.

The information processing unit 4 controls the operations of the transport unit 2 and the measuring units 31 and 32. The information processing unit 4 also detects errors, shows the error content on the display 42, and shows the electronic manual (operating manual) on the display 42 in accordance with instructions from the user, which will be described later.

Figure 2:
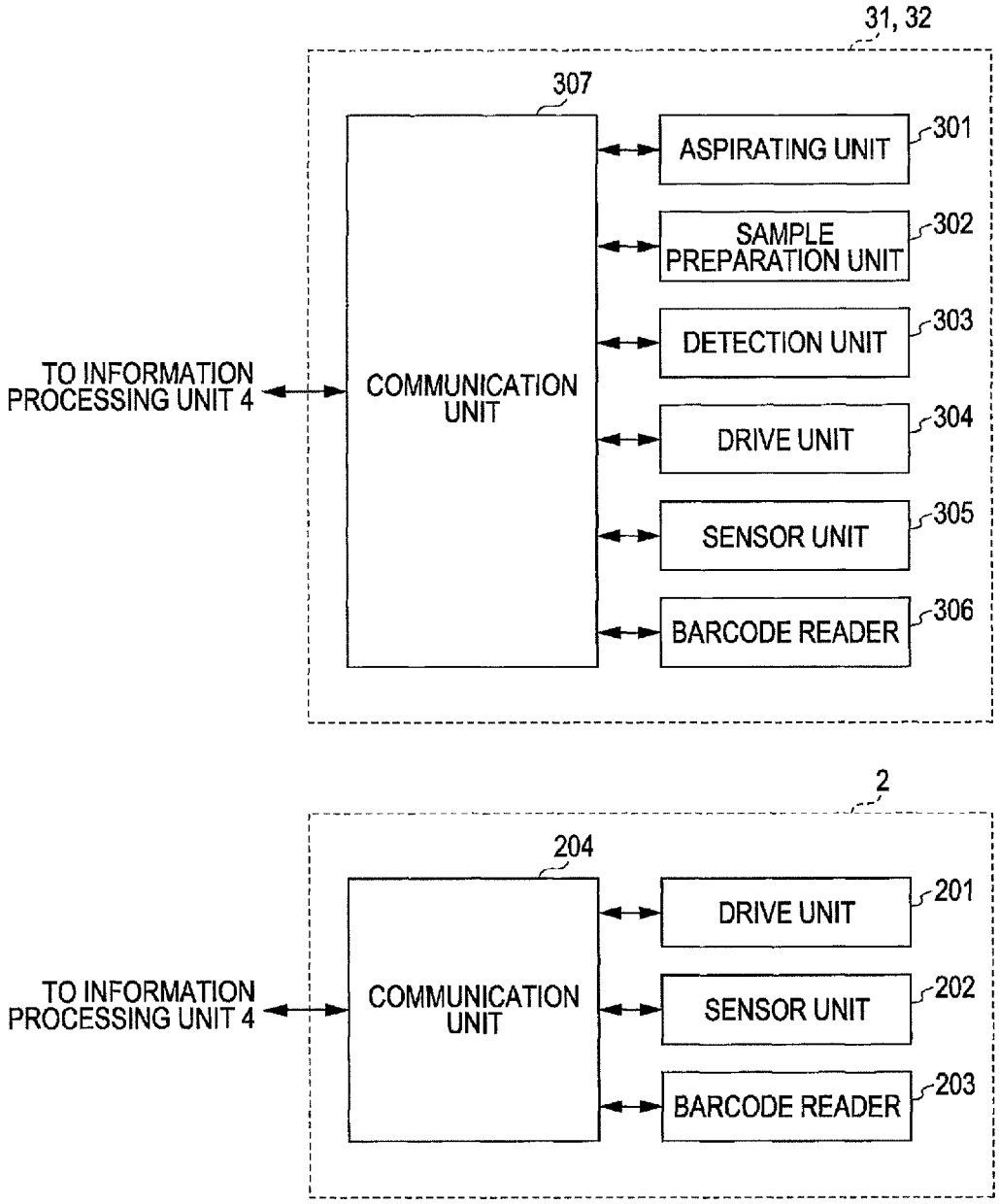
FIG. 2 briefly shows the structures of the measuring unit and the transport unit of the embodiment.

FIG. 2 briefly shows the structures of the transport unit 2 and the measuring units 31 and 32.

The transport unit 2 is provided with a drive unit 201, sensor unit 202, barcode reader 203, and communication unit 204.

The drive unit 201 includes a mechanism to transport the sample rack L within the transport unit 2, and the sensor unit 202 includes a sensor for detecting a sample rack L within the transport unit 2. The barcode reader 203 reads the barcode labels respectively adhered to the sample rack L and the sample containers T.

The communication unit 204 is connected to the information processing unit 4 so as to be capable of communication. Each part in the transport unit 2 is controlled by the information processing unit 4 through the communication unit 204. The signals output from each part in the transport unit 2 are transmitted to the information processing unit 4 through the communication unit 204.

The measuring units 31 and 32 are respectively provided with an aspirating unit 301, sample preparation unit 302, detection unit 303, drive unit 304, sensor unit 305, barcode reader 306, and communication unit 307. Note that the measuring units 31 and 32 are described only in terms of the measuring unit 31 since there structures are completely identical.

The aspirating unit 301 includes a mechanism for aspirating sample accommodated in the sample container T transported within the measuring unit 31. The sample preparation unit 302 has a plurality of reaction chambers. The sample preparation unit 302 mixes an aspirated sample and reagent within a reaction chamber to prepare a sample for measurement. The detection unit 303 measures the sample prepared by the sample preparation unit 302. The detection unit 303 has an optical detector for measuring white blood cells and nucleated red blood cells, which detects optical information (side fluorescent light signals, forward scattered light signals, and side scattered light signals) from the white blood cells and nucleated red blood cells in the sample as sample data. The detection unit 303 also has an electric RBC detector for measuring reticulocytes and platelets in the sample, by detecting electrical information from reticulocytes and platelets in a sample as sample data.

The drive unit 304 includes a mechanism for moving the sample container T within the measuring unit 31. The sensor unit 305 includes a sensor for detecting the sample container T within the measuring unit 31. The barcode reader 306 reads the barcode label adhered to the sample container T moved into the measuring unit 31.

The communication unit 307 is connected to the information processing unit 4 so as to be capable of communication. Each part in the measuring unit 31 is controlled by the information processing unit 4 through the communication unit 307. The signals output from each part in the measuring unit 31 are transmitted to the information processing unit 4 through the communication unit 307.

Figure 3:
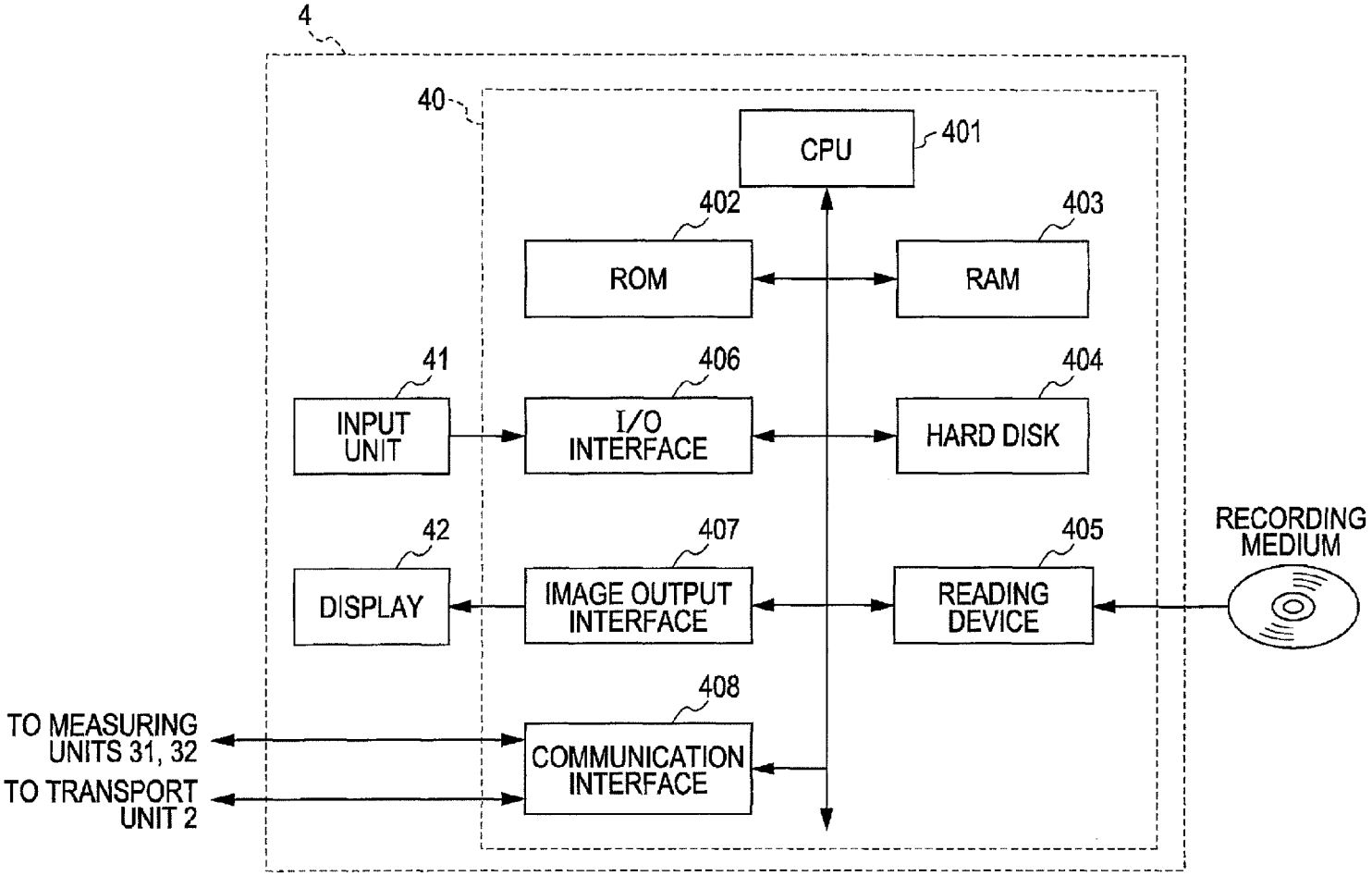
FIG. 3 shows the structure of the information processing unit of the embodiment.

FIG. 3 shows the structure of the information processing unit 4.

The information processing unit 4 is a personal computer configured by a main body 40, input unit 41, and display 42. The main body 40 has a CPU 401, ROM 402, RAM 403, hard disk 404, reading device 405, input/output interface 406, image output interface 407, and communication interface 408.

The CPU 401 is provided to execute a computer program stored in the ROM 402 and a computer program loaded in the RAM 403. The RAM 403 is used when reading the computer programs recorded in the ROM 402 and the hard disk 404. The RAM 403 is also used as a work area of the CPU 401 when executing these computer programs.

Various computer programs executed by the CPU 401, such as an operating system and application programs, as well as the data used in the execution of the computer programs are installed on the hard disk 404. That is, programs for analyzing the sample data received from the measuring units 31 and 32, generating measurement results for reticulocyte count and leukocyte count, and displaying the generated measurement results on the display 42 are installed on the hard disk 404. Also installed on the hard disk 404 are programs for storing the electronic manual of the sample processing apparatus 1, displaying the menu screen A1, help dialog D1, reagent replacement dialog D2 and the like (described later), and receiving input through these screens.

Note that the electronic manual of the present embodiment is a PDF (portable document format) file recording an operation method of the sample processing apparatus 1 in page sequence similar to a booklet-like operation manual recorded in chapters, paragraphs, sections and subsections. The electronic manual recorded a series of operation procedures in detail for the operations such as sample measurement, and dealing with trouble, using screen examples and diagrams of various types. The electronic manual may be prepared by digitizing an operation manual created in booklet form.

The reading device 405 is configured by a CD (compact disk) drive, DVD (digital video disk) drive or the like capable of reading computer programs and data recorded on a recording medium. Instructions and data are input to the information processing unit 4 by a user using the input unit 41, which includes a mouse and keyboard, through the connected I/O input interface 406. The image output interface 407 is connected to the display 42 configured by a display, and outputs image signals corresponding to video data to the display 42.

The display 42 shows images based on the input image signals. The display 42 shows various types of program images in addition to a menu screen A1, help dialog D1, and reagent replacement dialog D2, which are described later. Data are transmitted and received to/from the transport unit 2 and measuring units 31 and 32 via the communication interface 408. The CPU 401 monitors whether an error occurs in each part of the transport unit 2 and measuring units 31 and 32 through the communication interface in a manner to be described later.

Figure 4:
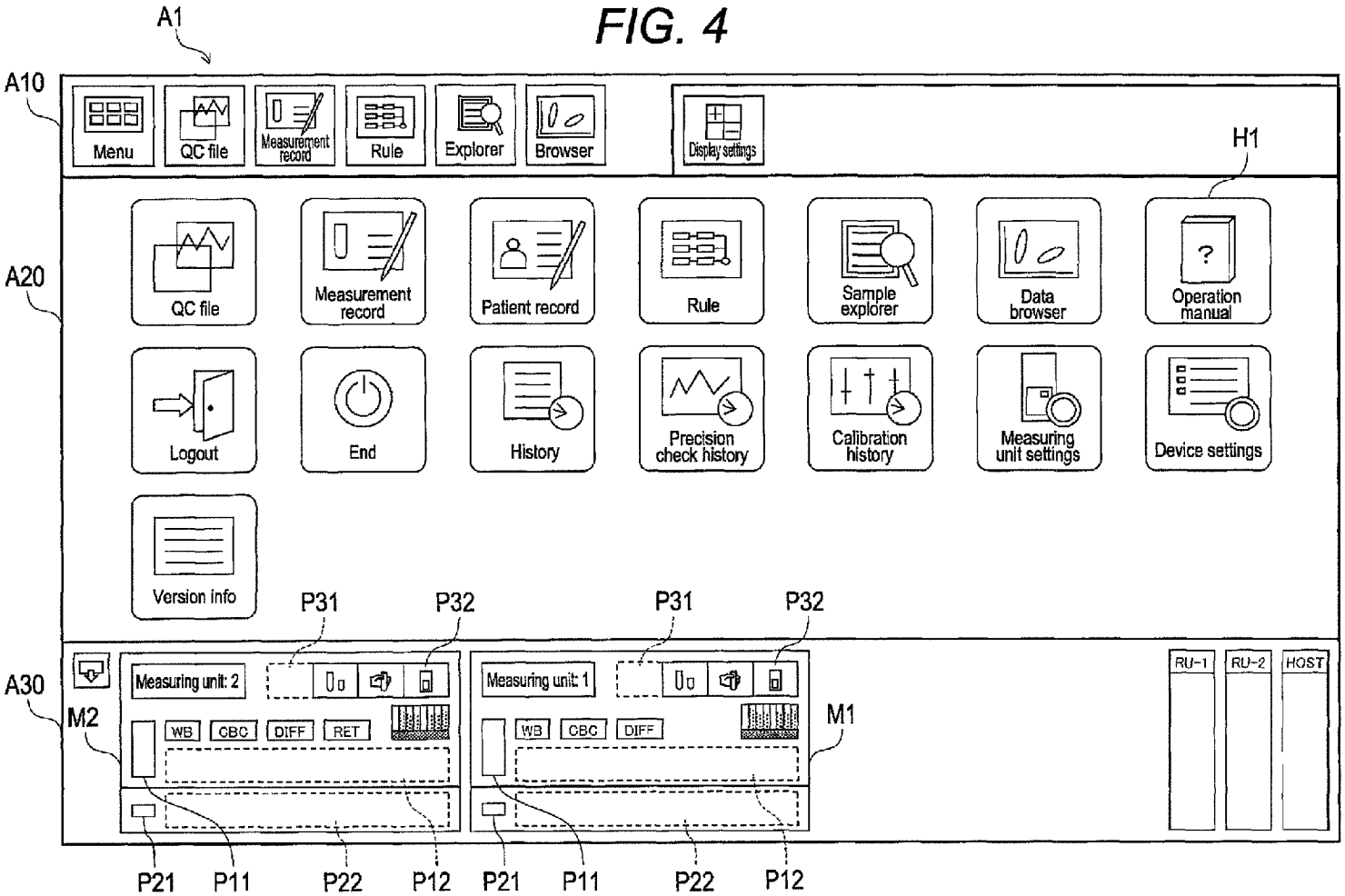
FIG. 4 shows a menu screen that is displayed on the display of the embodiment.

FIG. 4 shows the menu screen A1 as shown on the screen 42. Note that FIG. 4 shows the initial condition of the menu screen A1.

The menu screen A1 includes a tool bar region A10, main region A20, and measurement operation region A30.

The tool bar A10 includes a plurality of buttons. The tool bar A10 is normally shown at the top of the screen even though the display content of the menu screen A1 changes. The main region A20 includes a plurality of buttons for showing various menus. The user issues various instructions to the information processing unit 4 by pressing these buttons. Note that the main region A20 shows the plurality of buttons indicated in FIG. 4 in the initial state. The main region A20 shows an operation manual button H1 for displaying the electronic manual of the sample processing apparatus 1. When the operation manual button H1 is pressed, the electronic manual of the sample processing apparatus 1 is shown in the main region A20. Note that although the electronic manual may be shown in the main region A20 when operation manual display button D12 and the detail procedure display button D13 (described later) of the help dialog D1 are pressed, the operations of these buttons D12 and D13 are special and the electronic manual can be shown with an optional timing chosen by the user by operating the operation manual display button H1.

The measurement operation region A30 includes operation units M1 and M2 corresponding to the two measuring units 31 and 32. The operation units M1 and M2 have identical structures, which incorporate status alert units P11 and P21, error message display regions P12 and P22, error button P31 including an icon indicating an error warning, and operation unit menu button P32.

The status alert unit P11 shows green when the corresponding measuring unit is operating normally, and shows red when an error occurs in the measuring unit. The error message display region P12 shows an error message when an error occurs in the measuring unit. The status alert unit P21 shows green in the region of the transport unit 2 corresponding to this measuring unit when the unit is operating normally, and shows red when an error occurs in the transport unit 2. The error message display region P22 shows an error message in the region of the transport unit 2 when an error occurs. Note that in FIG. 4 the status alert units P11 and P21 are green and there are no error messages shown in the error message display regions P12 and P22 since no error has occurred.

The error button P31 is displayed when an error occurs in the corresponding measuring unit. When the error button P31 is shown, the help dialog D1 (refer to FIG. 5) is displayed at the top of the corresponding operation unit. Note that in FIG. 4 no error button P31 is shown since an error has occurred in the measuring units 31 and 32 and transport unit 2. The operation unit menu button P32 opens the operation menu screen (not shown in the drawing) which allows instruction to initiate various processes.

Figure 5:
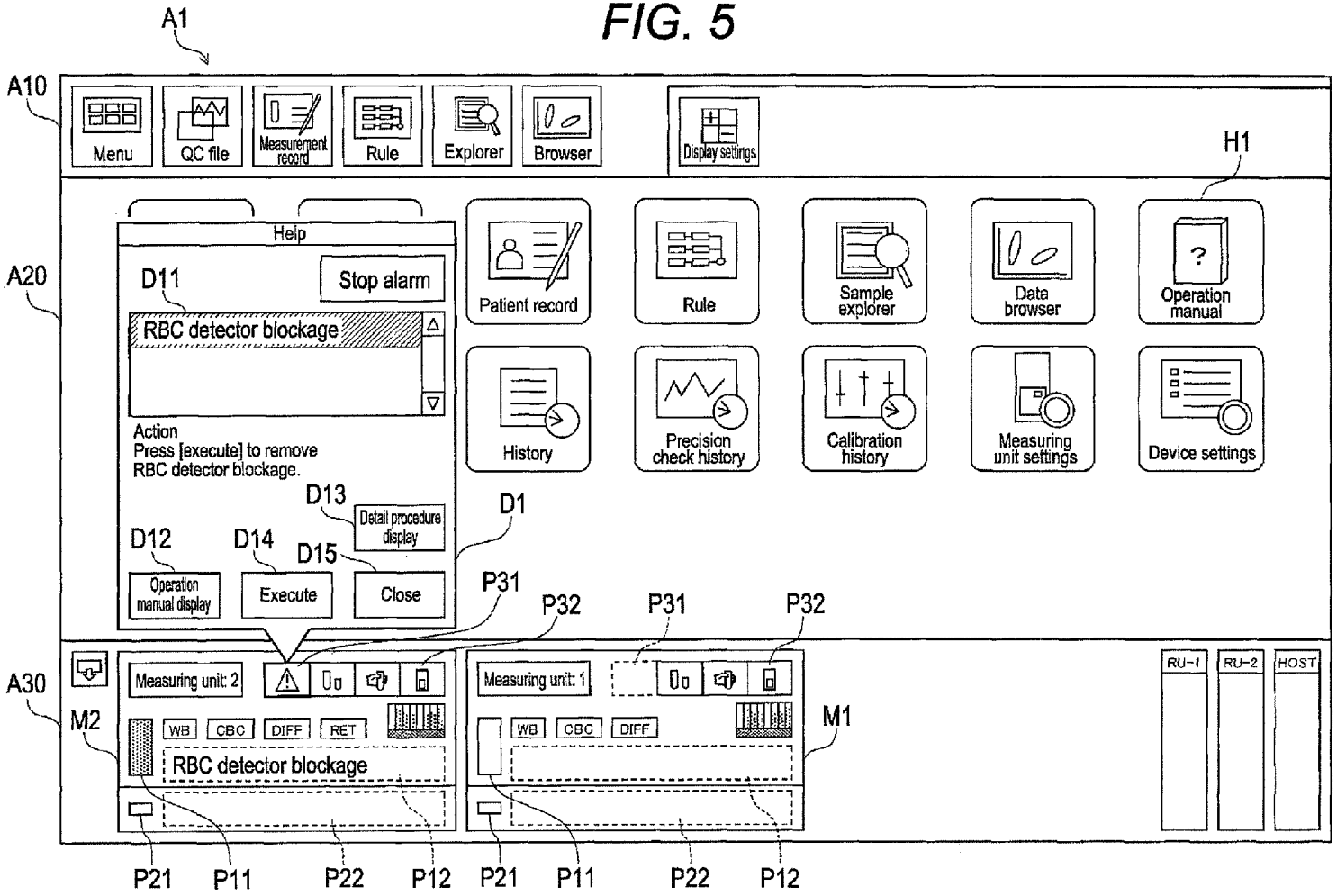
FIG. 5 shows the displayed content of the display when the help dialog is open in the present embodiment.

FIG. 5 shows the display content of the display 42 when the help dialog D1 is open. FIG. 5 shows the condition when an "RBC detector blockage" is generated in the measuring unit 32.

In the operation unit M2, the color of the status alert unit P11 becomes red when an error occurs in the measuring unit 32. An error message is also shown in the error message display region P12. When an error occurs in the measuring unit 32, an error button P31 is shown and a help dialog D1 is shown at the top of the operation unit M2.

The help dialog D1 includes an error message list D11, operation manual display button D12, detail procedure display button D13, execute button D14, and close button D15. An error item is shown, or, when a plurality of simultaneous errors occur, a plurality of error items are shown in the error message list D11.

When the operation manual display button D12 is pressed, the main region A20 shows the page of the electronic manual that records information such as the cause of the error, coping procedure and error recovery conditions for the error selected in the error message list D11. When the detail procedure display button D13 is pressed, the main region A20 shows the page of the electronic manual that records the coping method (operation procedure) for the error selected from the error message list D11. When the execute button D14 is pressed, a process is executed to cancel the error elected from the error message list D11. When the close button D15 is pressed, the help dialog D1 is closed.

For example, to cancel the RBC detector blockage, the user opens the cover 32a of the measuring unit 32, and performs a predetermined procedure to remove the RBC detector blockage, then presses the execute button D14. Hence, the RBC detector blockage error is eliminated, and the corresponding error item is erased from the error message list D11. When the entire error list is erased at this time, the error button P31 is erased and the help dialog D1 is closed, the color of the status alert unit P11 becomes green, and the error message is erased from the error message display region P12.

When an error item is shown in the error message list D11 and the close button D15 is pressed to close the help dialog D1, the error button P31 of the operation unit M2 remains shown since the error is not canceled. In this case, when the error button P31 is pressed, the help dialog D1 is again shown at the top of the operation unit M2.

Note that even when an error occurs in the measuring unit 31, the color of the status alert unit P11 of the operation unit M1 becomes red, an error message is shown in the error message display region P12, the error button P31 is shown, and the help dialog D1 is shown at the top of the operation unit M1.

Figure 6:
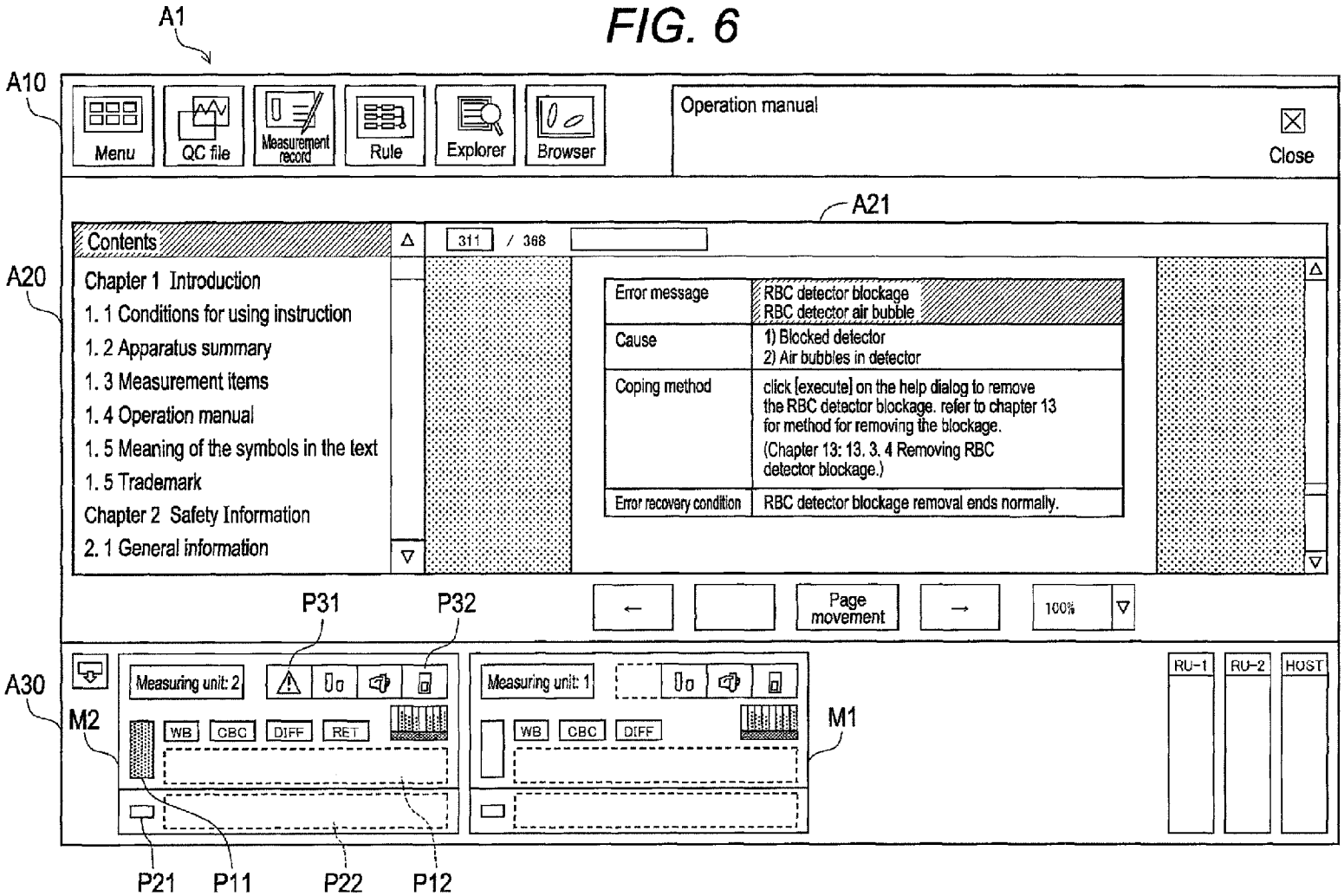
FIG. 6 shows the displayed content of the display when the operation manual display button is pressed in the help dialog in the present embodiment.

FIG. 6 shows the display content of the display 42 when the operation manual display button D12 is pressed in the help dialog D1 of FIG. 5.

When the user presses the operation manual display button D1 in the state shown in FIG. 5, the help dialog D1 is closed and the display region A21 is shown in the main region A20. As shown in FIG. 6, the display region A21 shows information explaining the error selected from the error message list D11 in this case. That is, when the operation manual display button D12 is pressed, the display region A21 shows the page of the electronic manual that records information such as the cause, coping procedure, and error recovery conditions of the object error (RBC detector blockage in FIG. 5).

Note that the electronic manual has a link function. When the operation manual display button D12 is pressed, the information corresponding to the error selected from the error message list D11 is read from the hard disk 404, and the appropriate page of the electronic manual is shown based on the link information. Link information designating the page of the electronic manual is associated with each error and the operation manual display button D12, and is stored on the hard disk 404.

The table of contents of the electronic manual are shown in the left side region of the display region A21, and the page of the electronic manual is displayed in the right side region of the display region A21. The left side region and the right side region are configured to allow vertical scrolling of the display content via the respective scroll bars.

Figure 7:
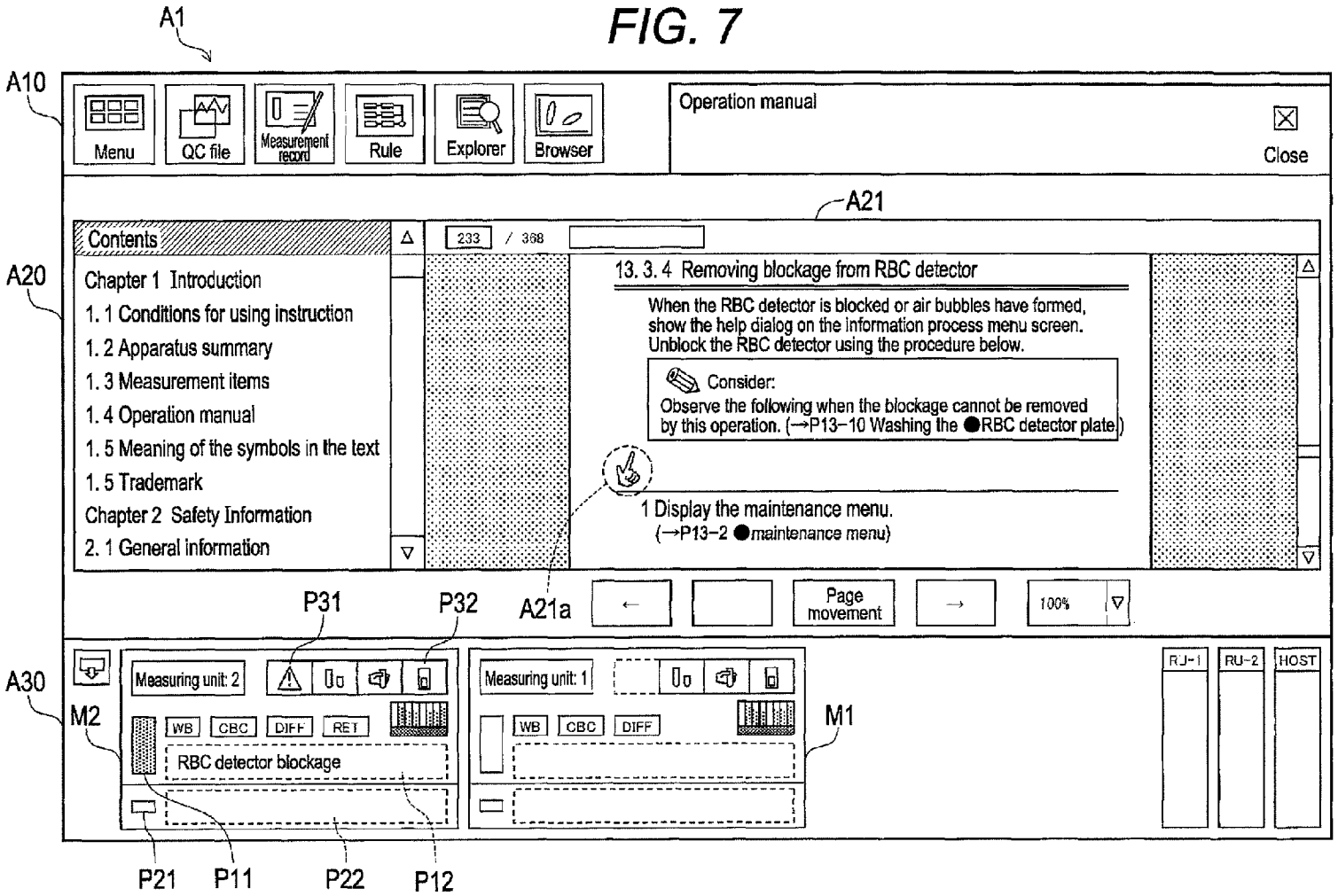
FIG. 7 shows the displayed content of the display when the detail procedure display button is pressed in the help dialog in the present embodiment.

FIG. 7 shows the display content of the display 42 when the detail procedure display button D13 is pressed in the help dialog D1 of FIG. 5.

When the user presses the detail procedure display button D13 in the state shown in FIG. 5, the help dialog D1 is closed and the display region A21 is shown in the main region A20. As shown in FIG. 7, in this case the display region A21 shows coping information (operation procedure to cancel the error) indicating the coping method for the error selected from the error message list D11. That is, when the detail procedure display button D13 is pressed, the display region A21 shows the page of the electronic manual that records the coping procedure (procedure to cancel the error) of the object error (RBC detector blockage in FIG. 5). Also in this case, the link information corresponding to the error selected from the error message list D11 is read from the hard disk 404, and the appropriate page of the electronic manual is shown based on the link information. Link information designating the page of the electronic manual is associated with each error and the detail procedure display button D13, and is stored on the hard disk 404.

Note that the electronic manual shown in the display region A21 includes the icon A21a designating the form of the instruction. The icon A21a is linked to a page in the electronic manual describing the item associated with icon A21a in greater detail. When the user presses the icon A21a, the item associated with the icon A21a is shown in the electronic manual where the information is recorded in greater detail. In this case, when the icon A21a is pressed, the link information held in the electronic manual is read and the page of the electronic manual is shown based on the link information. The electronic manual holds link information specifying the page within the electronic manual that corresponds to the icon.

The electronic manual shown in display region A21 shows a page including video with a more detailed explanation of the coping method (operation procedure for canceling the error) for the displayed error.

FIG. 8A shows a page of the electronic manual that contains video. The electronic manual has pre-embedded video information for detailed explanation of the coping method (procedure for canceling the error) for the RBC detector blockage, and a video display region A21b is provided for watching and operating the video. A control bar A21c is provided in the video display region A21b, so that a video of the operation procedure to cancel the RBC detector blockage is shown when the play button A21d is pressed in the control bar A21c. The user can change the video play position by operating the operation units of the control bar A21c.

Figure 8B:
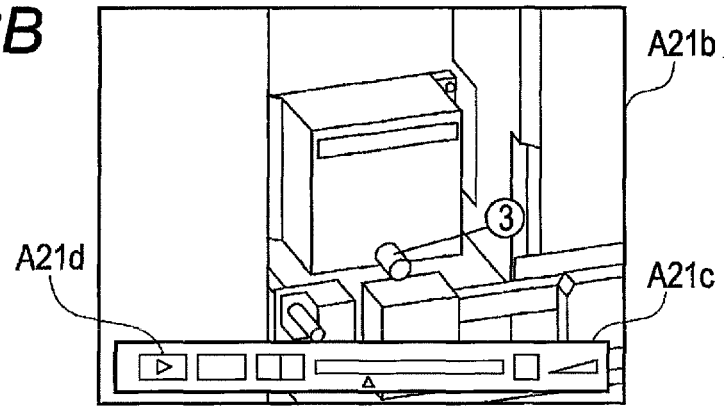
Figure 8C:
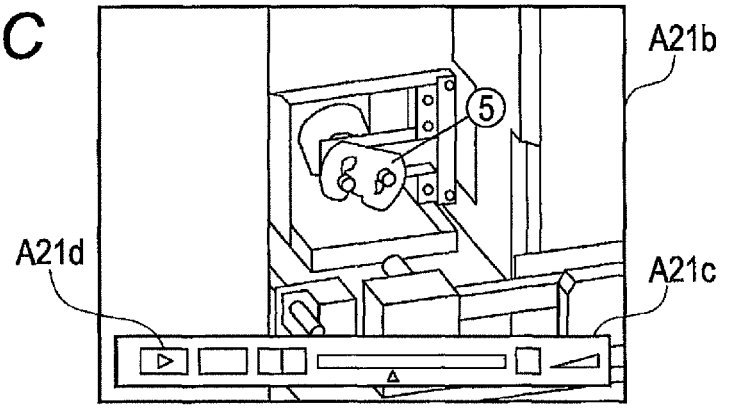
Figure 8D:
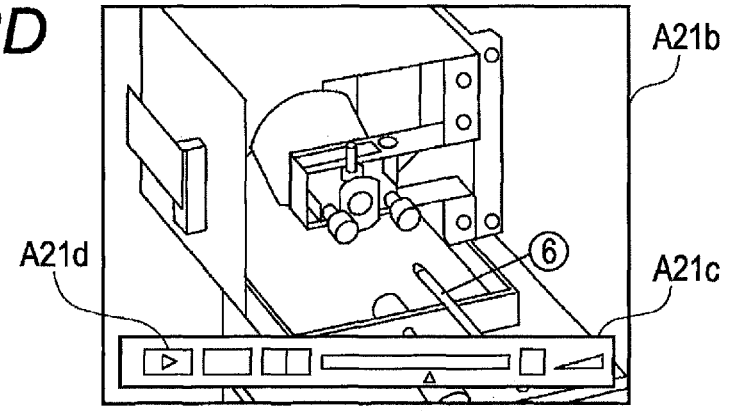

FIGS. 8B and 8C show the display content of the video display region A21b. The user can more easily cope with an error by knowing the operation procedure needed to cancel the error (in this case, RBC detector blockage) by referring to the video shown in the video display region A21b.

Figure 9:
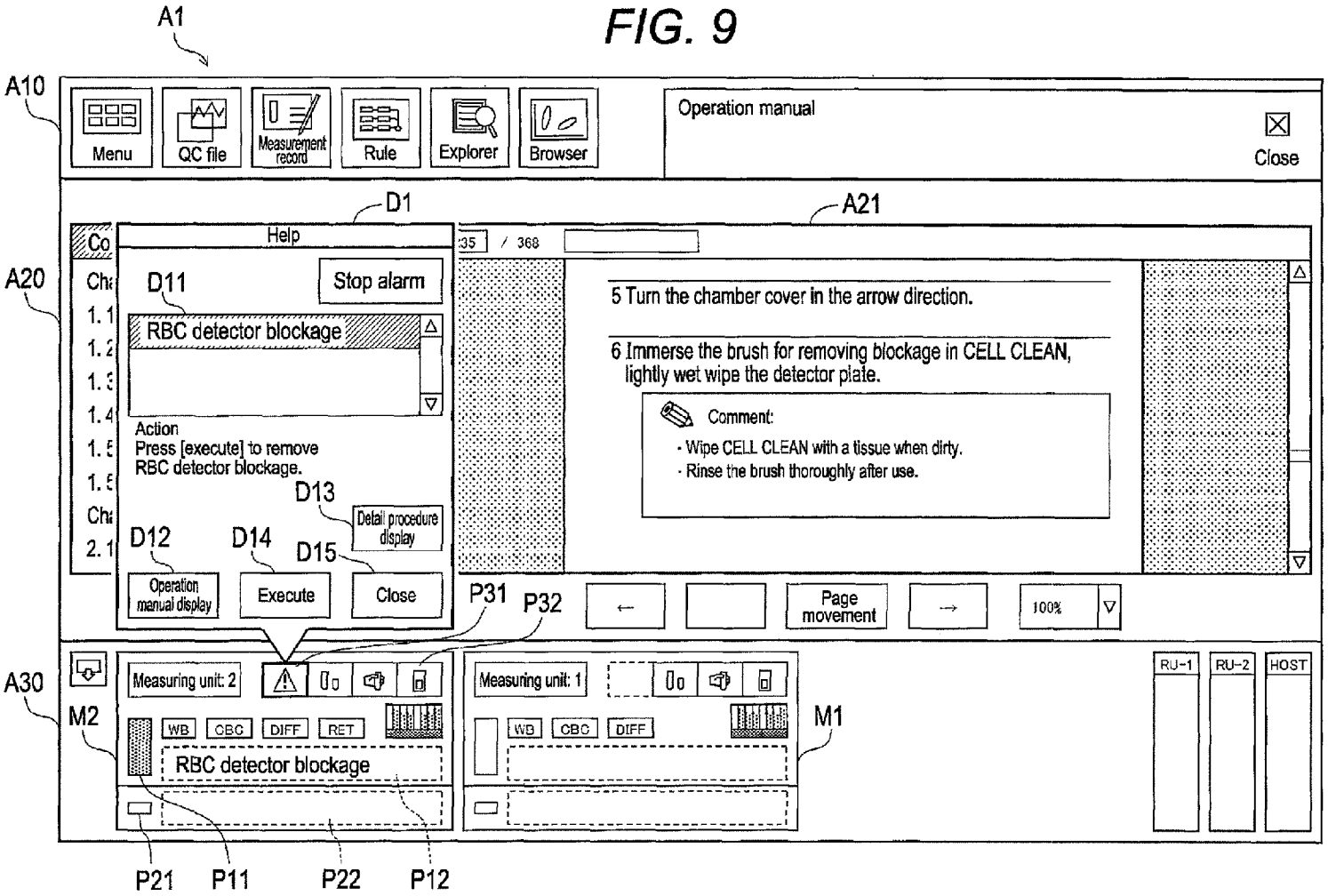
FIG. 9 shows the displayed content of the display when the help dialog and the display region are shown simultaneously in the present embodiment.

FIG. 9 shows the display content of the display 42 when the display region A21 and the help dialog D1 are shown simultaneously.

When the user presses the error button P31 while the display region A21 shows the coping method (operation procedure) for the error as shown in FIG. 7, the help dialog D1 is again shown, resulting in the condition shown in FIG. 9.

Hence, when the coping method (operation procedure) for the error and help dialog D 1 are shown together in the display region A21, the user can perform operations related to the help dialog D1 while viewing the display region A21. For example, when the user advances operations according to the electronic manual shown in display region A21 and later comes to the part indicating to press the execute button D14 in the electronic manual, the execute button D14 can be pressed smoothly. Therefore, the operation performance of the use is improved.

When the execute button D14 is pressed, the CPU 401 executes the automated washing of the RBC detector of the measuring unit as a recovery operation to recover from the trouble of the RBC detector blockage. In the automated washing, the inside of the RBC detector is washed automatically by flushing diluting liquid through the RBC detector a predetermined number of times.

Figure 10:
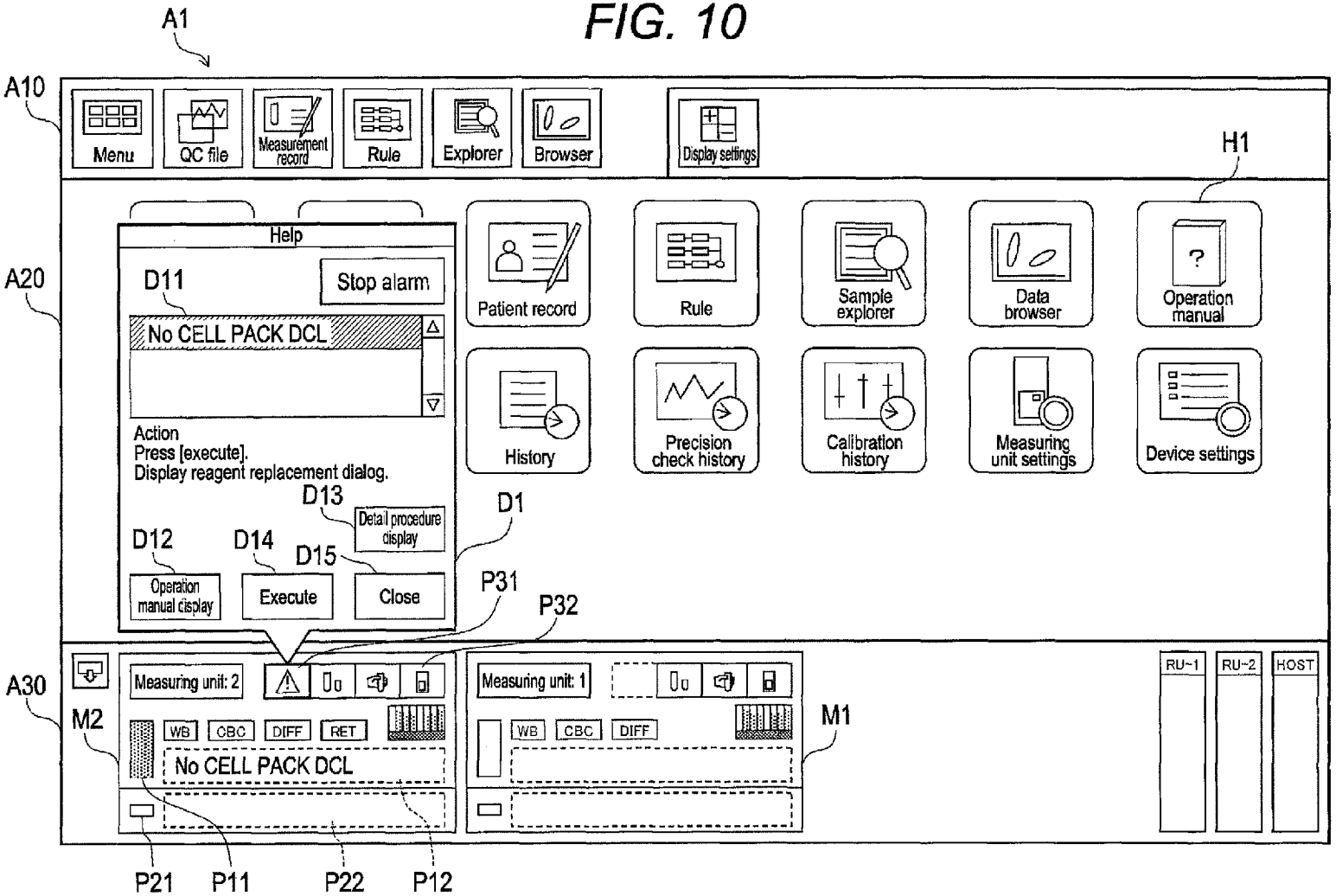
FIG. 10 shows the displayed content of the display when the help dialog is open based on reagent depletion in the present embodiment.

FIG. 10 shows the display content of the display 42 when the help dialog D1 is open based on the reagent depletion. FIG. 10 shows the condition when a "cell pack DCL depleted" is generated in the measuring unit 32.

In this case also, similar to FIG. 5, the color of the status alert unit P11 of the operation unit M2 turns red, an error message is shown in the error message display region P12, the error button P31 is shown, and the help dialog D1 is shown at the top of the operation unit M2.

Similar to FIG. 5, when the operation manual display button D12 is pressed, the main region A20 shows information explaining the error. When the detail procedure display button D13 is then pressed, the main region A20 shows the display region A21 indicating the coping method (procedure for canceling the error) for the error. When the execute button D14 is pressed, a process is executed to cancel the error elected from the error message list D11. When the close button D15 is pressed, the help dialog D1 is closed. When the error button P31 is pressed in the condition shown in FIG. 11, the help dialog D1 is shown as shown in FIG. 12.

Figure 12:
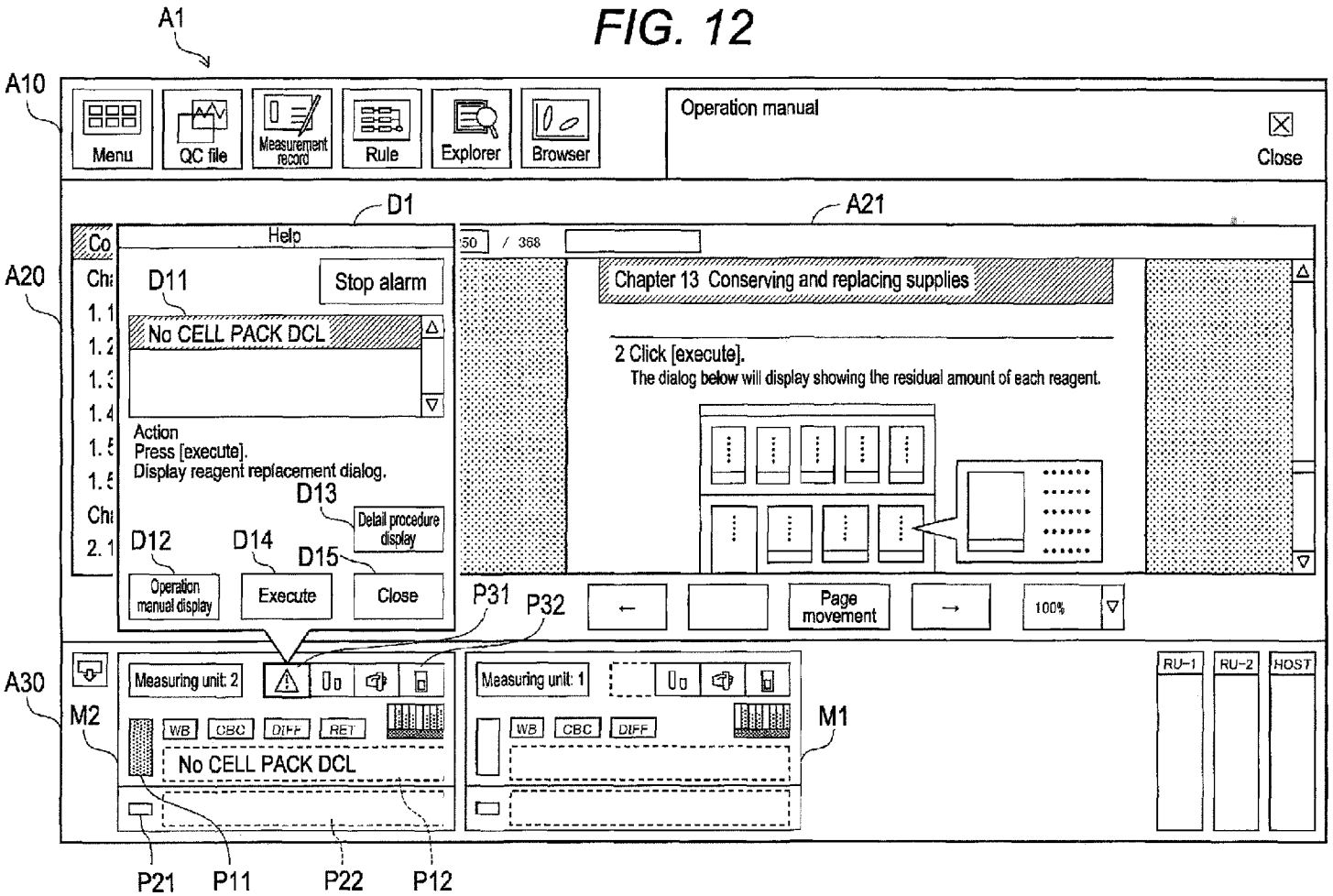
FIG. 12 shows the displayed content of the display when the help dialog and the display region are shown simultaneously in the present embodiment.
Figure 13:
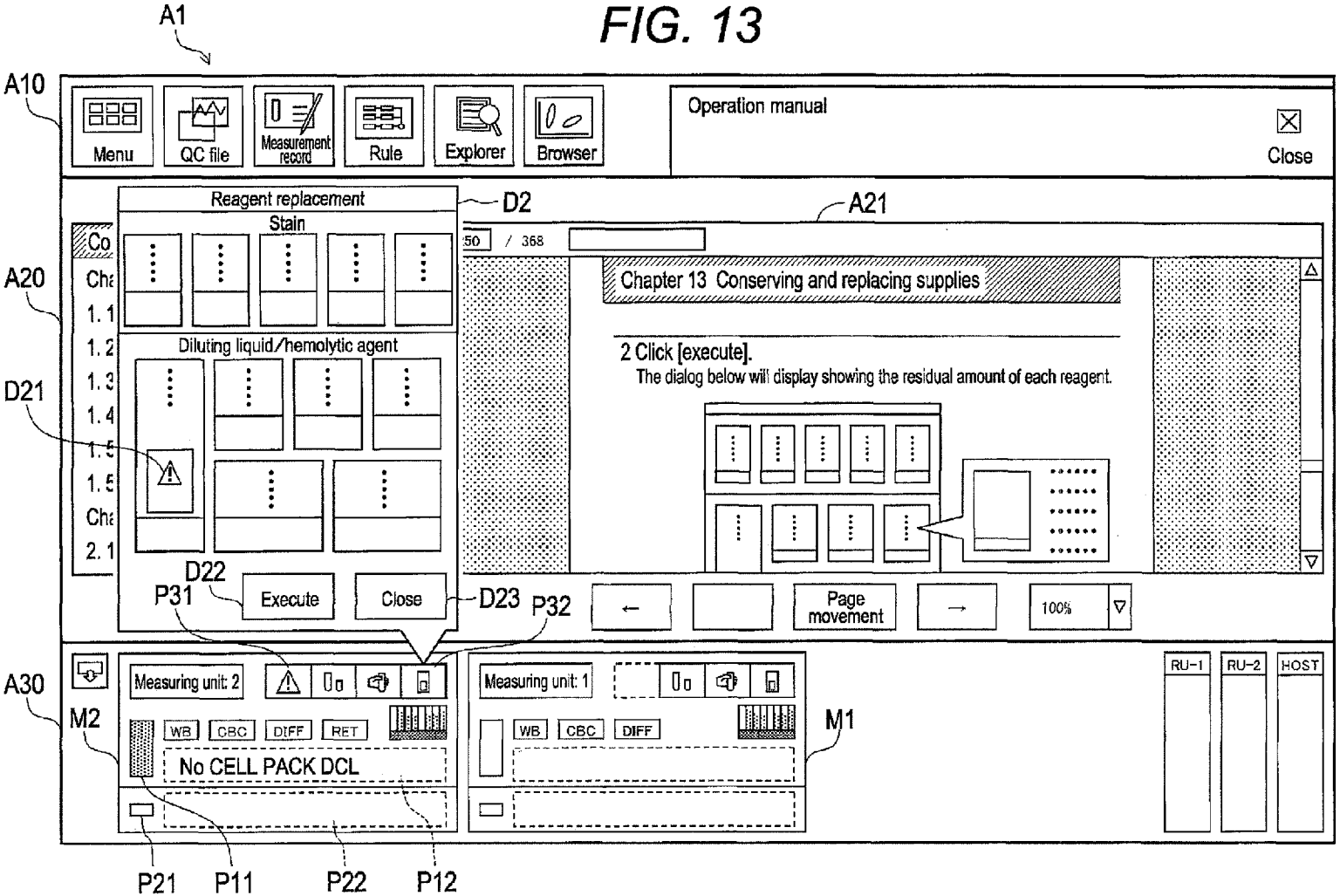
FIG. 13 shows the displayed content of the display when the execute button is pressed in the help dialog in the present embodiment.

FIG. 13 shows the display content of the display 42 when the execute button D14 is pressed in the help dialog D1 of FIGS. 10 and 12.

When the user pressed the execute button D14 in the condition shown in FIGS. 10 and 12, the help dialog D1 is closed and changed to the reagent replacement dialog D2. Note that the reagent replacement dialog D2 not only shows the execute button D14 of the help dialog D1 indicated in FIGS. 10 and 12, but also shows the operation unit menu screen (not shown in the drawings) by pressing the operation unit menu button P32 of the operation units M1 and M2.

As shown in FIG. 13, the reagent replacement dialog D2 shows a list of reagents installed in the measuring unit 32, and the residual amount in the reagent container is shown in the display region corresponding to each reagent. In FIG. 13, an icon D21 indicating insufficient residual reagent is shown in the display region corresponding to "cell pack DCL." Therefore, the user or other person can confirm whether there is insufficient residual amount of a reagent by confirming the icon D21.

Figure 11:
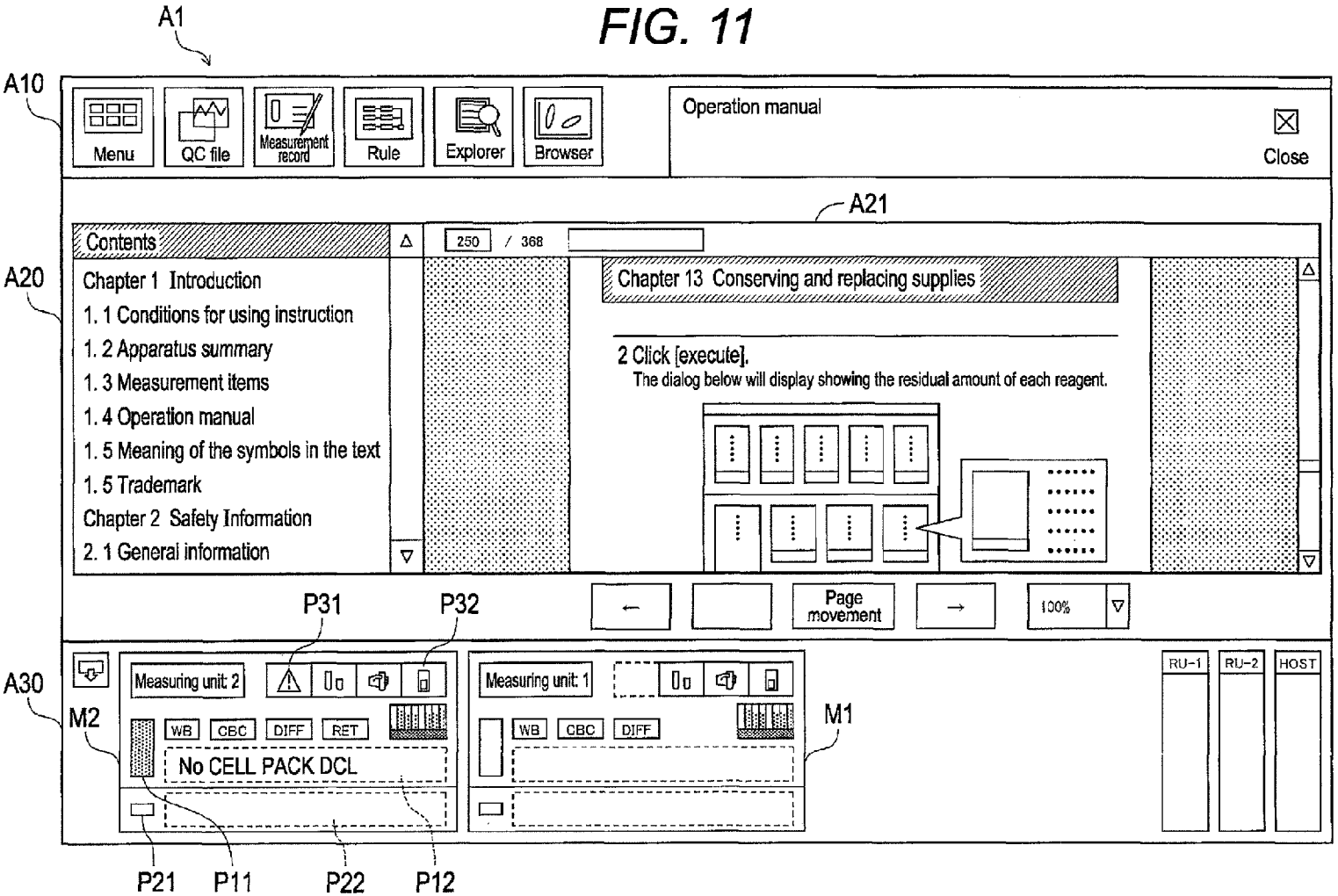
FIG. 11 shows the displayed content of the display when the detail procedure display button is pressed in the help dialog in the present embodiment.

The reagent replacement dialog D2 includes an execute button D22 and a cancel button D23. When the user erases "cell pack DCL depleted," the user opens the cover 32a of the measuring unit 32 and replaces the cell pack DCK reagent container, then presses the execute button D22. The operation procedure is described in a part of the electronic manual shown in the display region A21 as shown in FIG. 11. Therefore, the "cell pack DCK depletion" error is canceled the reagent replacement dialog D2 is closed, and the corresponding error item is erased from the error message list D11 of the help dialog D1. When the cancel button D23 is pressed, the reagent replacement dialog D2 is closed.

Figure 14:
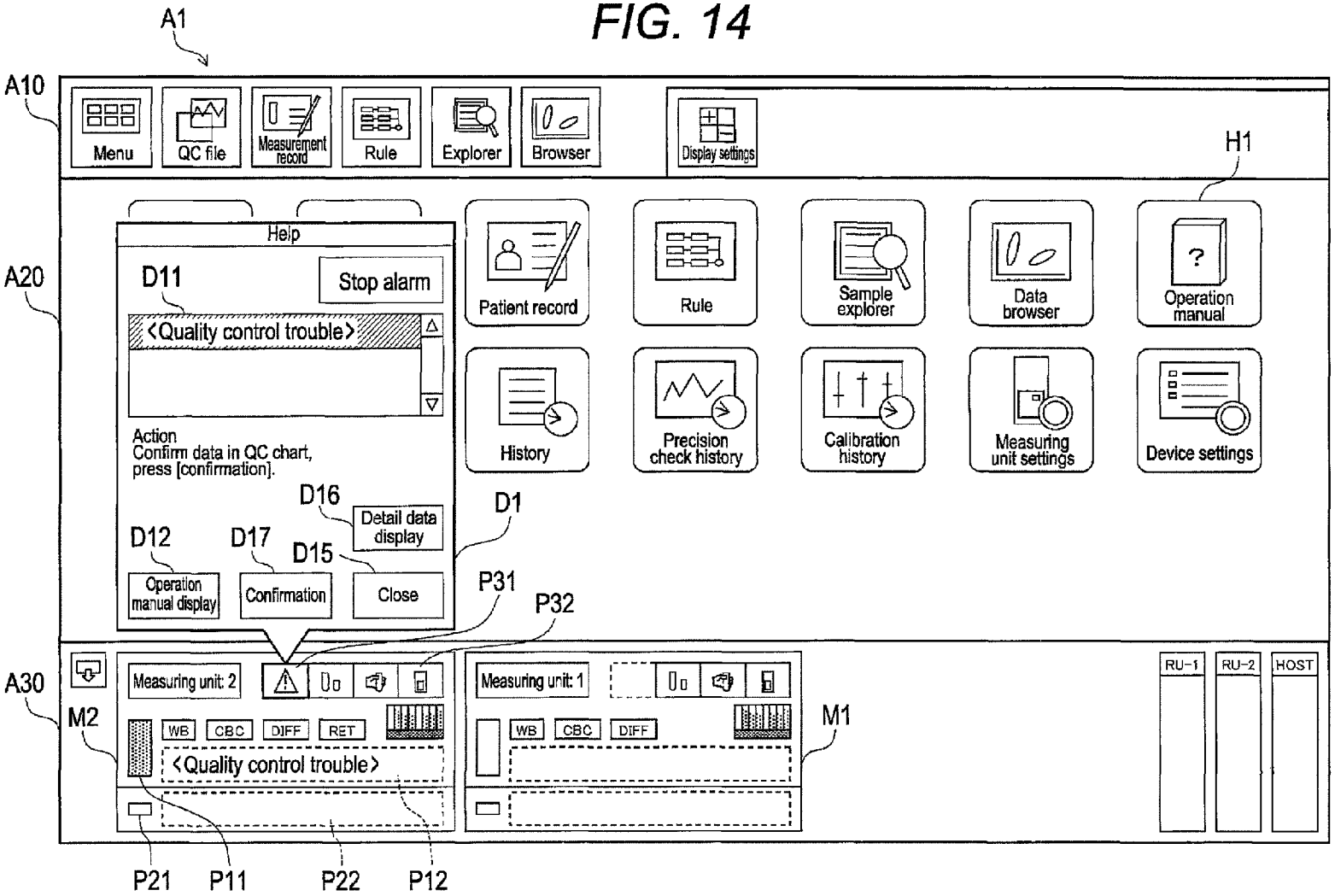
FIG. 14 shows the displayed content of the display when the help dialog is open based on quality control trouble in the present embodiment.

FIG. 14 shows the display content of the display 42 when the help dialog D1 is open based on quality control trouble. FIG. 14 shows the condition when quality control trouble occurs and "quality control trouble" is selected from the error message list D11 by including the results exceeding the normal range in the measurement results of a quality control substance in the measuring unit 32.

In this case also, similar to FIG. 5, the color of the status alert unit P11 of the operation unit M2 turns red, an error message is shown in the error message display region P12, the error button P31 is shown, and the help dialog D1 is shown at the top of the operation unit M2. The help dialog D1 in this case includes a detail data display button D16 and confirmation button D17 in addition to the operation manual display button D12 and close button D15 similar to the help dialog D1 of FIG. 5.

When the detail data display button D16 is pressed, a chart (refer to FIG. 15) relating to quality control is shown in the main region A20. When the confirmation button D17 is pressed, the quality control trouble error is canceled and the "quality control trouble" is erased from the error message list D11 and the help dialog D1 is closed since the user has confirmed the error.

Figure 15:
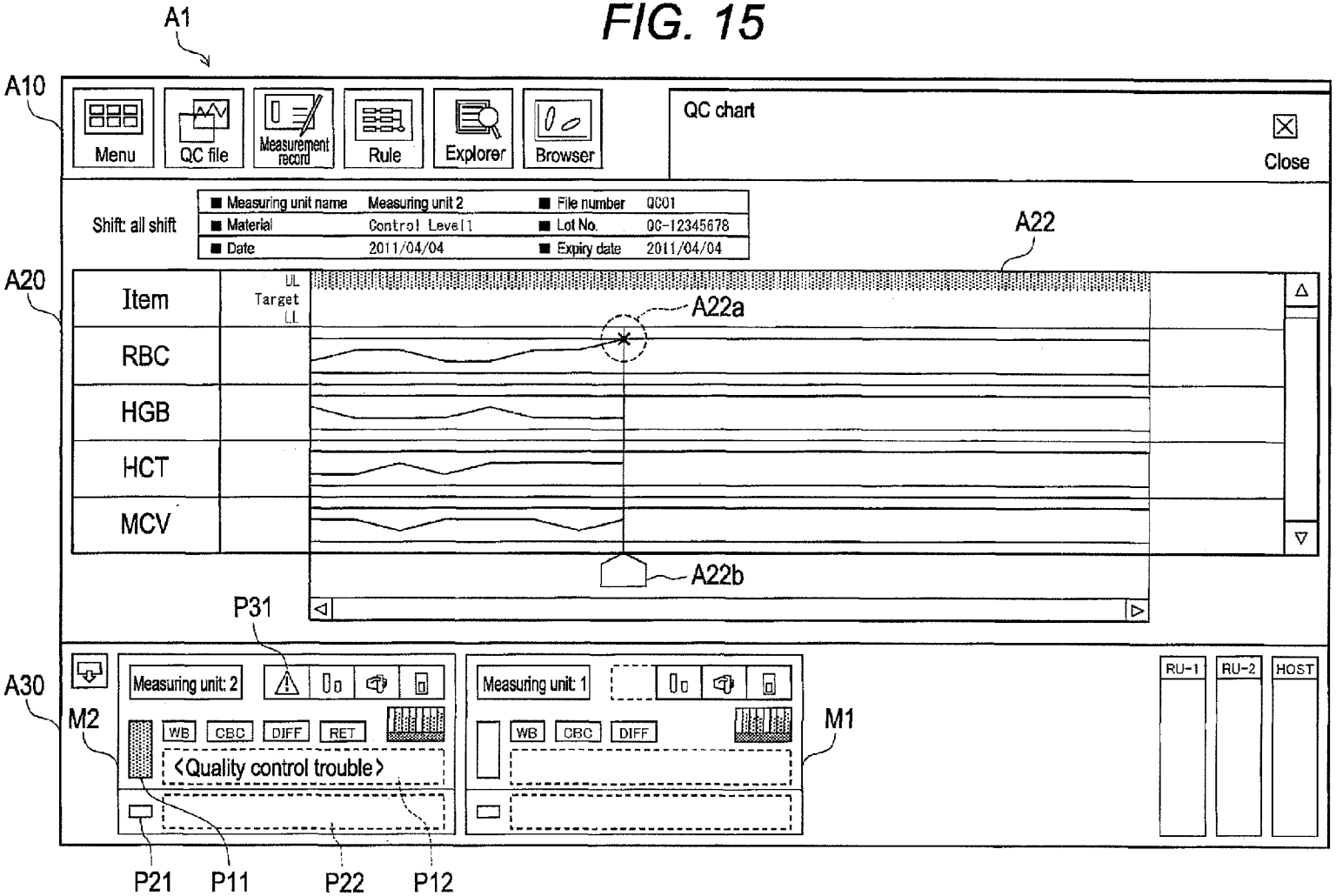
FIG. 15 shows the displayed content of the display when the detail data display button is pressed in the help dialog in the present embodiment.

FIG. 15 shows the display content of the display 42 when the detail data display button D16 is pressed in the help dialog D1 of FIG. 14.

When the user presses the detail data display button D16 in the state shown in FIG. 12, the help dialog D1 is closed and the display region A22 is shown in the main region A20. The display region A22 shows a chart indicating the history of measurement results in quality control for a plurality of items (RBC, HGB, HCT, MCV). Note that when quality control is performed, the measurement results of each measurement item are stored on the hard disk 404 together with the measurement time and date. When the detail data display button D16 is pressed, the old measurement data are read from the hard disk 40 and the chart shown in FIG. 15 is generated and displayed using the old measurement results read from disk and the current measurement result. When the chart indicating the history of quality control includes results that exceed normal ranges, an X-symbol icon A22a is shown at that position.

The cursor A22b is positioned at the measurement result that caused the quality control trouble at this time. In FIG. 13, a measurement result exceeding the normal range is generated in the current measurement item [RBC], and the cursor A22b is positioned at the icon A22a. Thus, the user can confirm the measurement item that generated the quality control trouble.

Figure 16A:
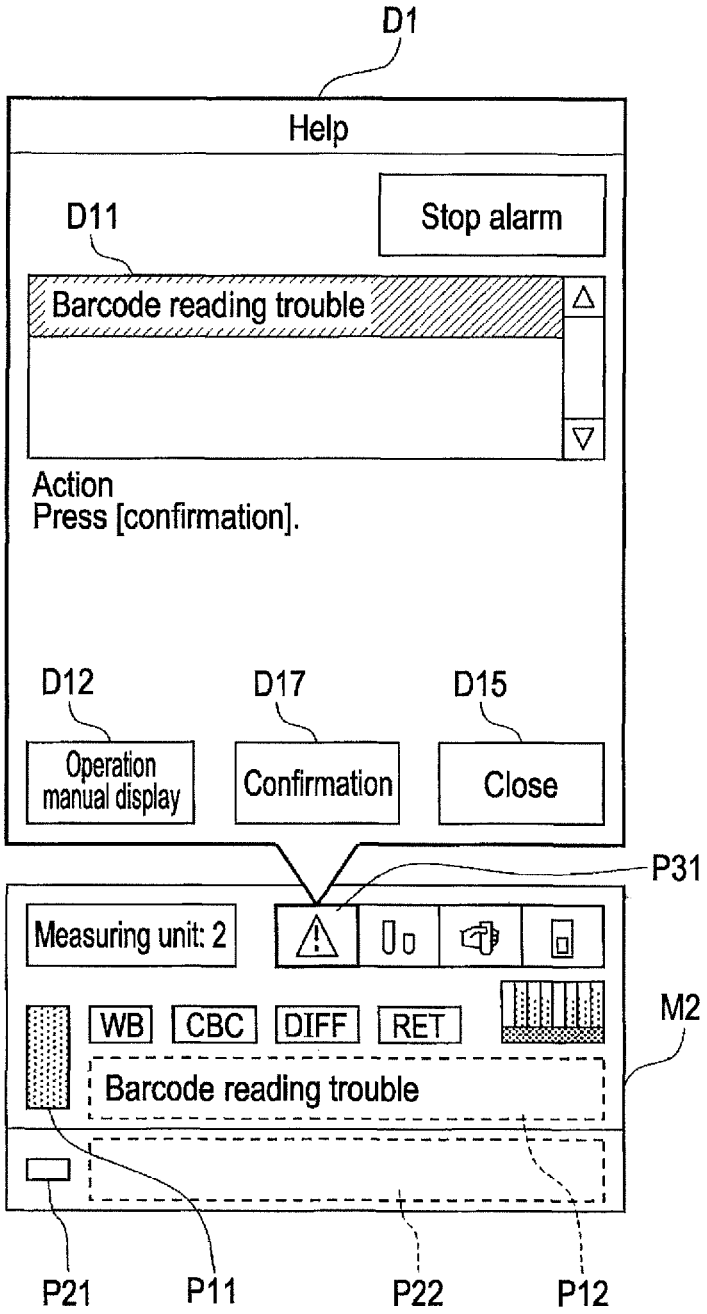
FIGS. 16A through 16C show the operation unit and the help dialog shown on the display when any of various errors occur in the present embodiment.
Figure 16B:
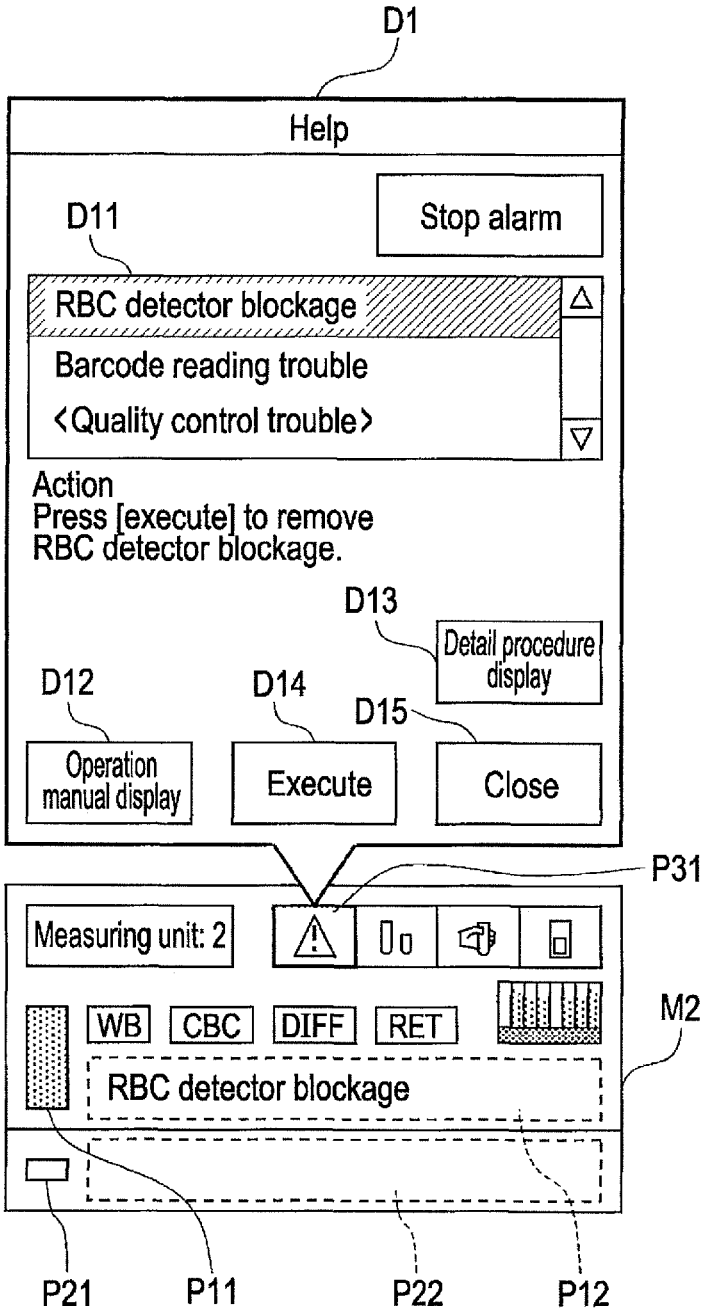
Figure 16C:
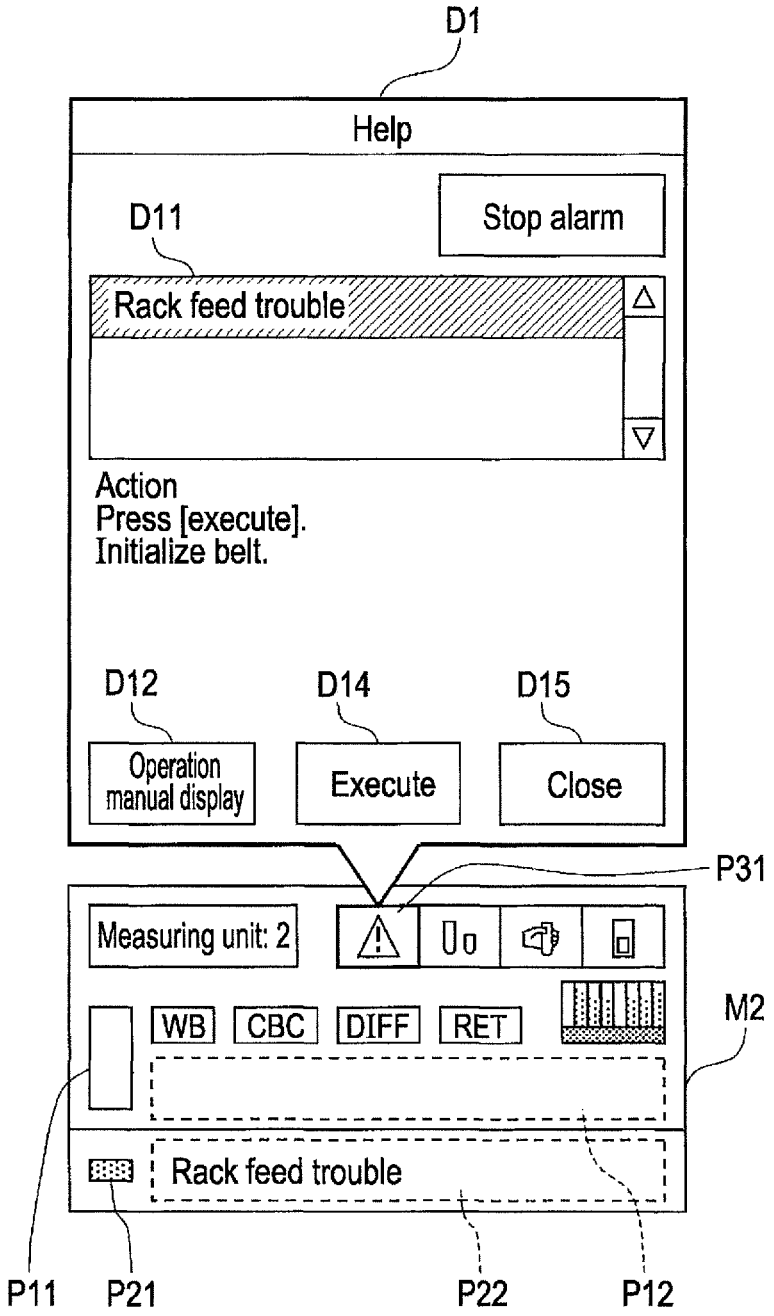

FIGS. 16A through 16C show the help dialog D1 and operation unit M2 that are shown on the display 42 when various errors occur in the measuring unit 32 and transport unit 2.

FIG. 16A shows the condition when barcode reading trouble occurs in the measuring unit 32 and barcode reading error is selected from the error message list D11.

The help dialog D1 in this case shows an operation manual display button D12, close button D15, confirmation button D17, detail procedure display button D13, and detail data display button D16. When the confirmation button D17 is pressed, the error is canceled since the user has confirmed that a barcode reading error has occurred. When the operation manual display button D12 is pressed, information explaining the error (barcode reading trouble) is shown.

FIG. 16B shows the condition when a plurality of errors occur in the measuring unit 32, and "RBC detector blockage" is selected from the error message list D11. Note that the error message display region P12 shows error items at the uppermost level of the error message list D11.

As shown in FIG. 16B, when the "RBC detector blockage" is selected from the error message list D11, the help dialog D1 shows the operation manual display button D12, detail procedure display button D13, execute button D14, and close button D15 similar to FIG. 5. When the user selects "barcode reader trouble" in the situation shown in FIG. 16B, the help dialog D1 shows the operation manual display button D12, close button D15, and confirmation button D17 similar to FIG. 16Z. When the user selects "quality control trouble" in the situation shown in FIG. 16B, the help dialog D1 shows the operation manual display button D12, close button D15, detail data display button D16, and confirmation button D17 similar to FIG. 14.

Thus, with the exception of the operation manual display button D12 and the close button D15, the buttons arranged in the help dialog D1 change according to the error item selected from the error message list D11. That is, the information associated with the error items and displayed buttons is stored on the hard disk 404 of FIG. 3. Hence, the user can rapidly perform an operation when she wants to know the coping method (operation procedure) for an error and when wanting to confirm the data of the cause of an error. When the user is unsure of the coping method (operation procedure) needed for an error, a detail procedure display button D13 is shown in the help dialog D1. The user can therefore confirm the predetermined procedure to use to cancel the error.

FIG. 16C shows the condition when an error occurs in a region of the transport unit 2 corresponding to the measuring unit 32 and "rack feed trouble" is selected from the error message list D11.

The help dialog D1 in this case shows an operation manual display button D12, execute button D14, and close button D15, and the detail procedure display button D13, and detail data display button D16 are not shown. When the execute button D14 is pressed, belt (not shown in the drawing) initialization is performed for the rack transporter 23, and the error is canceled.

Figure 17:
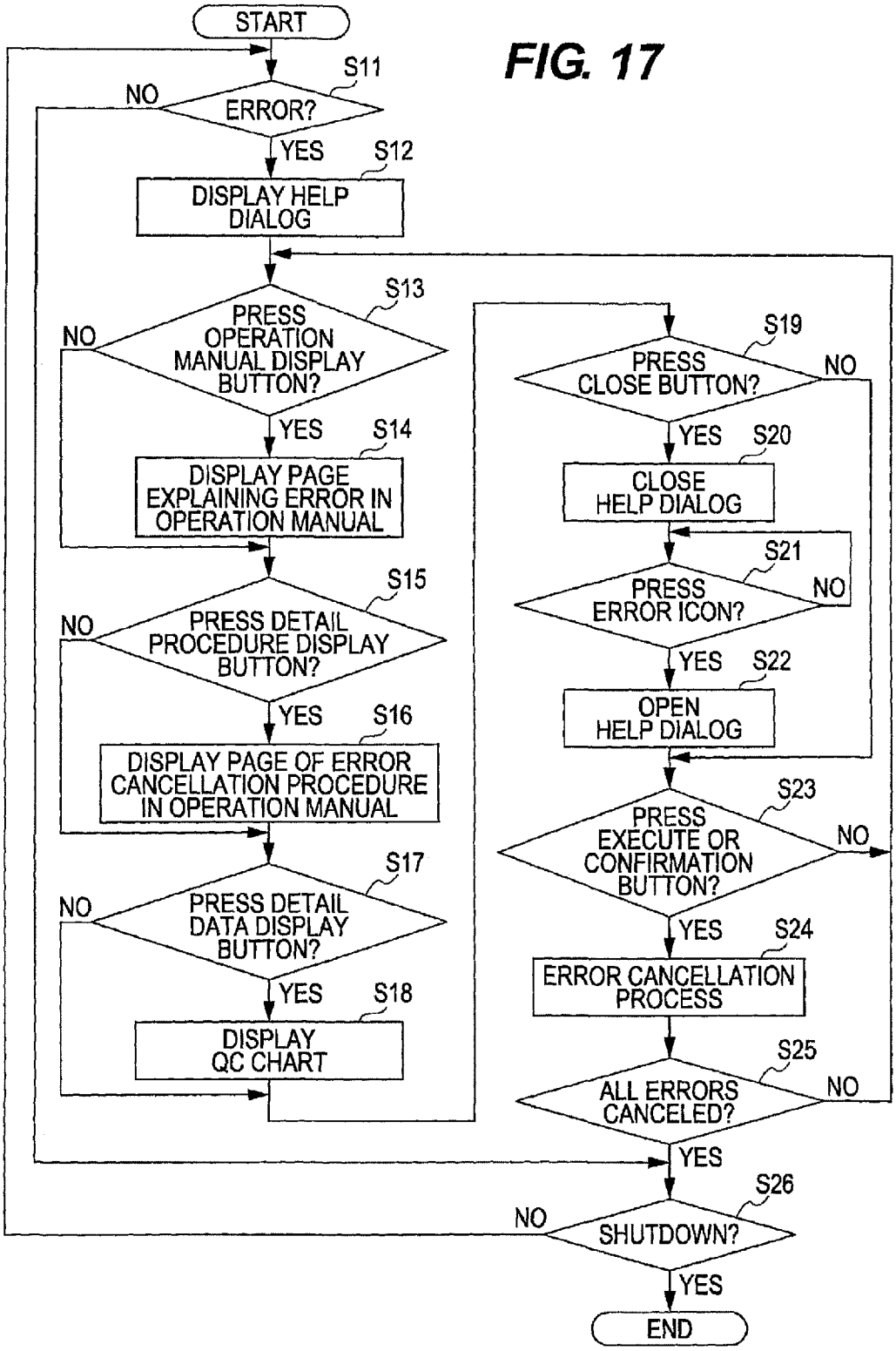
FIG. 17 is a flow chart of the process executed by operating the help dialog in the present embodiment.

FIG. 17 is a flow chart of the processes performed by operating the help dialog D1.

The CPU 401 of the information processing unit 4 monitors whether an error occurs in the units (measuring units 31 and 32, and transport unit 2) within the sample processing apparatus 1 (S11). When an error is detected (S11: YES), the process advances to S12. When no error is detected (S11: NO), the processes of Sll through S25 are repeated until shutdown is performed (S25: YES).

When an error occurs, the CM 401 shows the help dialog D1 on the display 42. The process is performed as follows according to the user operation of the buttons arranged in the help dialog D1.

When the operation manual display button D12 is pressed (S13: YES), the CPU 401 shows in the main region A20 the page of the electronic manual recorded for the error (S14). When the detail procedure display button D13 is pressed (S15: YES), the CPU 401 shows in the main region A20 the page of the electronic manual recording the coping method (operation procedure) for the error (S16). When the detail data display button D16 is pressed (S17: YES), the CPU 401 shows in the main region A20 the chart indicating the history of measurement results for quality control (S18).

When the close button D15 is pressed (S19: YES), the CPU 401 closes the help dialog D1 (S20). Thereafter, when the error button P31 is pressed (S21: YES), the CPU 4012 again shows the help dialog D1 (S22). When either the execute button D14 or confirmation button D17 is pressed (S23: YES), the CPU 401 executes the process to cancel the error (S24). Alternatively, when either the execute button D14 or confirmation button D17 is not pressed (S23: NO), the process returns to S13. When all errors included in the error message list D11 are canceled (S25: YES), the process advances to S26. Alternatively, when all errors are not canceled (S25: NO), the process returns to S13.

According to the present embodiment, a user can show the page of the electronic manual that describes the coping method (operation procedure) of an error in the main region A20 by pressing the detail procedure display button D13 when the user does not know the coping method (operation procedure) for the trouble (error). Therefore, the user does not need to specially search for the relevant part describing the coping method for the error all through the operation manual stored in booklet format within the facility. The user can execute the process to cancel the error by pressing the execute button D14. The burden on the user regarding the error cancellation process is therefore reduced.

According to the present embodiment, since the page of the electronic manual recording the coping method for the error can be shown by pressing the detail procedure display button D13 in the help dialog D1 when an error has been detected, there is no need to show the page of the error by pressing the operation manual button H1 shown in the main region A20 of the menu screen A1. The burden on the user is therefore reduced.

According to the present embodiment, the help dialog D1 shows the detected trouble (error) on the error message list D11 together with the detail procedure display button D13 and execute button D14. Thus, the user can confirm the error, show the coping method (operation procedure) for the error, and execute the process for canceling the error.

According to the present embodiment, when the user does not know the coping method (operation procedure) for the detected trouble (error), the coping method (operation procedure) can be shown in the main region A20, confirmed, then the error can be canceled by pressing the execute button D14. When the user knows the coping method (operation procedure) for the detected error, the error can be immediately canceled by pressing the execute button D14 without showing the coping method (operation procedure). The burden on the user regarding the error cancellation process is therefore reduced.

Although the present invention is described by way of the examples of the above embodiments, the present invention is not limited to the above embodiment.

For example, although the example of the embodiment pertains to blood used as the object of measurement, urine may also be an object of measurement. That is, the present invention may be applied to a sample processing apparatus for examining urine, or may also be applied to a clinical sample processing apparatus for examining other clinical samples.

Although the above embodiment is described by way of example of a recovery operation from trouble executed by the measuring unit, that is, washing of the interior of the RBC detector is performed by the measuring unit when an RBC detector blockage has occurred, the present invention is not limited to this arrangement. The recovery operation executed by the measuring unit also may be, for example, moving a hand member to the origin position when trouble occurs in the operation of the hand member that removes the sample container T from the sample rack L on the rack transporter 23.

Although the above embodiment is described in terms of showing a page of the electronic manual that records the coping method (operation procedure) for an error in the main region A20 by the user pressing the detail procedure display button D13, the present invention is not limited to this arrangement. The page of the electronic manual also may be automatically shown in the main region A20 without pressing the detail procedure display button D13.

For example, when only one trouble is detected in the sample processing apparatus 1 and the help dialog D1 is shown, the page of the electronic manual recording the coping method for the trouble may be automatically shown in the main region A20. Specifically, when one trouble is detected while the screen is displayed as shown in FIG. 4, the page of the electronic manual recording the coping method may be shown in display region A21 as shown in FIG. 9 without user operation.

Even when a plurality of trouble is detected in the sample processing apparatus 1, the priority sequence of the plurality of trouble is determined and the help dialog D1 displayed, and the page of the electronic manual pertaining to the coping method for the highest priority trouble may be automatically shown in the main region A20. In this case, when the highest priority trouble is canceled, the page of the electronic manual shown in the main region A20 may be automatically changed to the page of the electronic manual pertaining to the coping method of the next highest priority trouble.

Figure 18:
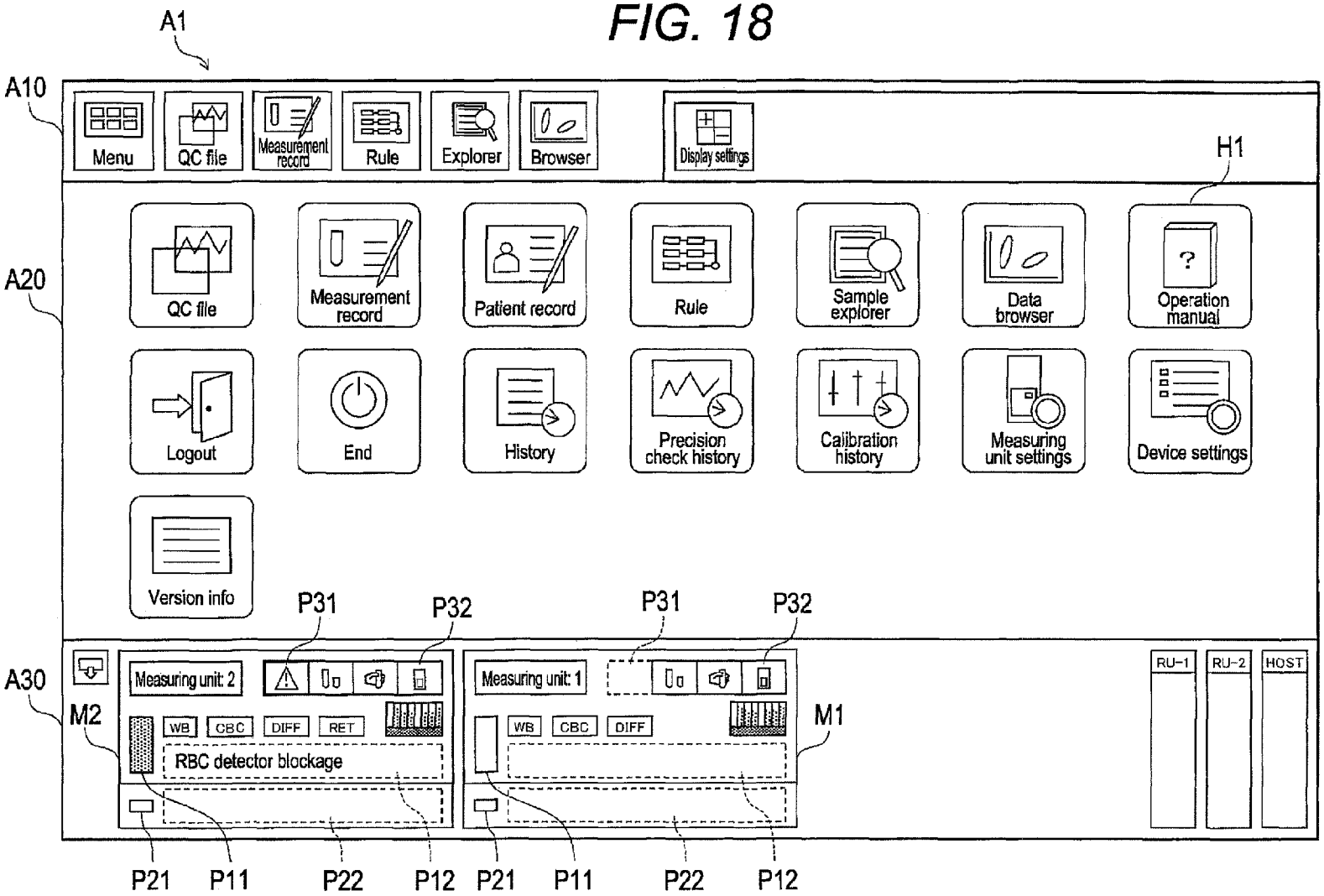
FIG. 18 shows a modification of the menu screen that is displayed on the display when trouble is detected in the embodiment.

When trouble has been detected in the present embodiment, the help dialog D1 is shown in addition to the error button P31 is shown, the color of the status alert unit P11 turns red, and error message is shown in the error message display region P12 as shown in FIG. 5. However, the present invention is not limited to this arrangement inasmuch as, when trouble has been detected, only the error button P31, status alert unit P11, error message display region P12 may be shown without showing the help dialog D1, or shown as in the above embodiment. In this case, when the error button P31 is pressed, the help dialog D1 may be shown (refer to FIG. 5) similar to the above embodiment. When the error button P31 is pressed in the condition shown in FIG. 18, the help dialog D1 may be shown together with automatically showing the page of the electronic manual pertaining to the coping method in the display region A21.

The embodiment of the present invention may be variously modified and adapted insofar as such modification and adaptation is within art as described in the scope of the claims.

What is claimed is:

1. A *clinical* sample processing apparatus, comprising:

a sample processing unit configured to process a *clinical* sample;

a display;

a computer connected [with] *to* the sample processing unit and [with] *to* the display, and [comprising] *including* a non-transitory memory [configured to store] *having* an electronic manual *stored therein* for the *clinical* sample processing apparatus, *the electronic manual includes a plurality of pages, at least some of the pages describing operation procedures for measuring a clinical sample and at least some of the pages describing procedures for dealing with several errors including a predefined number of different types of errors in an error message list,* wherein the non-transitory memory [is] further [configured to store] *includes* link information [designating a part] *stored therein that associates the pages* of the electronic manual with [respects to each type] *predefined number* of [error in association with] *different* types of errors, the computer is programmed to [determine that an error has occurred in] *monitor a status of* the sample processing unit and, *upon a detection of an error at the sample processing unit, display an error message along with a button image operable to call up the electronic manual on the display,*

*the computer is further programmed* to read out the link information from the non-transitory memory [upon determination that an error has occurred] *in response to operation of the button*, and [makes the display to show the part] *to create a view of a page* of the electronic manual [designated] with *a reference to* the link information [according to the] *that directs the view to a particular page associated with a type of detected error, wherein the link information directs the view to a page describing an operation procedure for dealing with the first* type of [the occurred] error, *when a first type of error is detected, and to a page describing an operation procedure for dealing with a second type of error, when the second type of error is detected; and*

*the computer is further programmed to show on the display a view of the electronic manual, and to allow a user to scroll to other pages of the electronic manual.*

2. The *clinical* sample processing apparatus of claim 1, wherein the computer is further programmed to show, on the display, a first screen image that shows [information related to] *the status of the* sample processing *unit*, and to show the [relevant part] *particular page* of the electronic manual on the first screen image when the error has occurred.

3. The *clinical* sample processing apparatus of claim 1, [further comprising an input device,] wherein the computer is [connected with the input device, and is] further programmed to:

[make the] display [to show] a second screen image [that includes a trouble display region] showing a list of errors *that* occurred in the sample processing unit[, and an operation procedure instruction button] *in which one of the errors are selectable*; *and* read out the link information from the non-transitory memory [when the] *in response to* operation [procedure instruction button] of the [second screen] *button* image [is operated by the input device;

make the display] *operable* to [show the part of] *call up* the electronic manual [designated with the link information according to the type] *upon selection* of [the error selected in the list of] *one of the* errors.

4. The *clinical* sample processing apparatus of claim 3, wherein the computer is further programmed to [show the second screen] *display a cancel button* image [to include a cancel process instruction part for instructing execution of a cancel process to cancel the error] *with the error message*; and the computer is further programmed to execute [the] *a* cancel process when the cancel [process instruction part of the second screen image] *button* is [manually] operated[by the input device].

5. The *clinical* sample processing apparatus of claim 4, wherein the computer is further programmed to [show, on the display, the second screen image together with the relevant part of the electronic manual, and to receive the operation of the cancel process instruction part] *display the cancel button image* while the [relevant part] *particular page* of the electronic manual is shown on the display.

6. The *clinical* sample processing apparatus of claim 4, wherein the sample processing unit is configured to process the *clinical* sample using reagents in a plurality of reagent containers; and the computer is further programmed to determine an occurrence of an [sufficiency] *insufficiency* of a reagent remaining in one of the reagent containers, and to execute a display process, as the cancel process, to show on the display a screen image that distinguishably shows the reagent container where the insufficiency of reagent has occurred.

7. The *clinical* sample processing apparatus of claim 3, wherein the sample processing unit is configured to measure the *clinical* sample[;], and the computer is further programmed to:

determine an occurrence of an abnormality of a measurement result of the *clinical* sample measured by the sample processing unit;

[show, on the] display[, the second screen image to include a detail information instruction part when the] *an error message regarding an* abnormality of [the] *a* measurement result [has occurred;] and *a button image operable to view a detail information of the abnormality; and*

[show, on the] display[,] a measurement result screen image showing the abnormal measurement result[, when] *upon receipt of an operation of the button to view* the detail information[instruction part is manually operated by the input device].

8. The *clinical* sample processing apparatus of claim 2, further comprising an input device, wherein the computer is connected with the input device, and is further programmed to:

show, in the first screen image, a manual display instruction part for instructing a display of the electronic manual[,]*;* and show the electronic manual on the display even when the error has not been detected in the sample processing unit in response to an operation of the manual display instruction part by the input device.

9. The *clinical* sample processing apparatus of claim 1, further comprising an input device, wherein the computer is connected with the input device and is [further] programmed to play an animation file that is a part of the electronic manual when the animation file is executed by an operation of the input device.

10. The *clinical* sample processing apparatus of claim 3, wherein the computer is further programmed to:

*read out the screen image from the non-transitory memory;* display the first screen image to include a main region for displaying information relating to the sample processing, and a sub region that is different from the main region;

[show] *display* an error object in the sub region when an error has occurred; and

[show] *display* the second screen image so as to be overlapped on the first screen image when the error object is manually operated by the input device.

11. The *clinical* sample processing apparatus of claim 10, wherein the computer is further programmed to:

display the second screen image to include a no-display object; and erase the second screen image on the display when the no-display object is manually operated by the input device, and again show the second screen image so as to be overlapped on the first screen image when the error object of the sub region is manually operated by the input device.

12. The *clinical* sample processing apparatus of claim 1, wherein the computer is further programmed *to read out the link information from the non-transitory memory and* to automatically show the relevant part of the electronic manual on the display when information indicating a content of the error is shown on the display.

13. The *clinical* sample processing apparatus of claim 1, wherein the sample processing unit comprises*:* a sample preparation unit configured to prepare a measurement sample from a blood and a reagent; and a detector configured to detect characteristic information from a blood cell contained in the measurement sample prepared by the sample preparation unit, wherein the computer is further programmed to obtain a number of blood cells in the blood based on a detection data obtained by the detector.

*14. A method for guiding execution of an error-solving operation, the method executed by a computer of a clinical sample processing apparatus to implement steps comprising:*

*processing and analyzing the clinical sample by the clinical sample processing apparatus;*

*detecting an error in the clinical sample processing apparatus;*

*upon detection of the error, displaying, on a display of the clinical sample processing apparatus, an error message and a button image operable to call up an electronic manual;*

*upon operation of the button image, accessing a non-transitory memory of the clinical sample processing apparatus that stores the electronic manual for the clinical sample processing apparatus including a plurality of pages, at least some of the pages describing operation procedures for measuring a clinical sample and some of the pages describing operation procedures for dealing with several errors including a predefined number of different types of errors, and link information that links errors in the clinical sample processing apparatus to relevant pages of the electronic manual to operation procedures for dealing with the error, wherein accessing the non-transitory memory comprises locating the link information stored in the non-transitory memory in relation to the error, and*

*creating a view on the display of a particular page of the electronic manual that is designated by the link information, wherein the particular page appearing in the view differs depending upon the type of error; and*

*displaying the created view of the electronic manual in a scrollable manner.*

*15. The method according to claim 14, further comprising displaying an operation status of the clinical sample processing apparatus in a first screen area, wherein responsive to a detection of the error, changing the displayed operation status to an alerting status for alerting the error.*

*16. The method according to claim 14, further comprising:*

*displaying a dialogue screen on the display that comprises a list of errors which have previously occurred and at least one of an operation manual display button image or a recovery procedure display button image; and*

*receiving a selection input for a selected error among the listed errors, wherein displaying the relevant pages of the electronic manual comprises:*

*(i) responsive to operation of the operation manual display button image, displaying the relevant section of the electronic manual linked by the link information to the selected error, wherein the relevant section comprises information on a cause of the selected error; or*

*(ii) responsive to an operation of the recovery procedure display button image, displaying the relevant section of the electronic manual linked by the link information to the selected error, wherein the relevant section comprises information on procedures for recovering from the selected error.*

*17. The method according to claim 16, wherein, responsive to an operation of the recovery procedure display button image, displaying the relevant section of the electronic manual further comprises displaying a video showing the procedures for recovering from the selected error.*

*18. The method according to claim 14, further comprising displaying a list of reagents accessible by the clinical sample processing apparatus with an identification of one of the reagents that indicates that the identified reagent is running out.*

*19. The method according to claim 14, further comprising displaying a quality control record showing quality control test results with an identification of one of the quality control test results that indicates an abnormality.*

*20. A clinical sample processing apparatus, comprising:*

*a sample processing unit configured to process a clinical sample;*

*a display; and*

*a computer connected to the sample processing unit and to the display, and comprising a non-transitory memory having an electronic manual for the clinical sample processing apparatus stored therein, the electronic manual is deployed in the non-transitory memory to include a plurality of pages, at least some of the pages describing operation procedures for measuring a clinical sample and at least some of the pages describing operation procedures for dealing with several types of errors,*

*wherein the non-transitory memory further includes link information designating a part of the electronic manual with respect to the operation procedure for dealing with each of the several types of errors, and*

*the computer is programmed to:*

*determine that an error has occurred in the sample processing unit;*

*upon determination that the error has occurred, display a screen image that includes the error, an operation procedure instruction button image and a message indicating user action for dealing with the error;*

*read out the link information from the non-transitory memory responsive to an operation of the operation procedure instruction button image;*

*create a view of a page of the electronic manual with reference to the link information that directs the view to a particular page associated with a type of the error, wherein the link information directs the view to a page describing the operation procedure for dealing with the type of error; and*

*display the created view of the electronic manual, that allows a user to scroll to other pages of the electronic manual.*

*21. The clinical sample processing apparatus of claim 20, wherein the non-transitory memory includes screen image information, and the computer is programmed to read out the screen image from the non-transitory memory and automatically display the screen image when the error has occurred.*

*22. A clinical sample processing apparatus comprising:*

*a sample processing unit configured to process a clinical sample using reagents in a plurality of reagent containers;*

*a display; and*

*a computer connected to the sample processing unit and to the display, and comprising a non-transitory memory having an electronic manual for the clinical sample processing apparatus stored therein, the electronic manual including a series of operation procedures for measuring a clinical sample and for dealing with different types of errors in page sequence,*

*wherein the non-transitory memory further includes link information designating a part of the electronic manual with respect to the operation procedure for dealing with each of the different types of errors,*

*the computer is programmed to determine that an error has occurred in the sample processing unit and to read out the link information from the non-transitory memory, and display the part of the electronic manual with respect to the operation procedure for dealing with a type of the error designated with the link information,*

*wherein the computer is further programmed to:*

*determine an insufficiency of reagent remaining in one of the reagent containers;*

*upon determination of the insufficiency of reagent, display a reagent replacement dialogue screen that includes a list of the reagent containers, a remaining amount of reagent in each of the reagent containers, and an identification of the reagent container having the insufficiency of reagent; and*

*upon receipt of an input from a user after the reagent is replaced, terminate the reagent replacement dialogue.*

*23. A clinical sample measuring apparatus, comprising:*

*a sample measuring unit configured to measure a clinical sample;*

*a display; and*

*a computer connected to the sample measuring unit and to the display, and comprising a non-transitory memory having an electronic manual for the clinical sample processing apparatus stored therein, the electronic manual includes a series of operation procedures for measuring a clinical sample and for dealing with each type of error in page sequence,*

*wherein the non-transitory memory further includes link information designating a part of the electronic manual with respect to the operation procedure for dealing with different types of errors,*

*the computer is programmed to determine that an error has occurred in the sample measuring unit and to read out the link information from the non-transitory memory, and display the part of the electronic manual with respect to the operation procedure for dealing with a type of error designated with the link information,*

*wherein the non-transitory memory includes test results obtained by the sample measuring unit,*

*the computer is further programmed to:*

*when a quality control test result of a quality control substance has exceeded a normal range, display a dialogue screen including a detail data display button image and an error display region indicating a quality control error; and*

*responsive to an operation of the detail data display button image, display a chart showing a history of quality control test results of the quality control substance.*

*24. The clinical sample measuring apparatus of claim 23, wherein the computer is further programmed to display the chart with an identification of any quality control test results that is not within a predesignated normal range.*

* * * * *